US009487591B2

(12) United States Patent
Takayanagi et al.

(10) Patent No.: US 9,487,591 B2
(45) Date of Patent: *Nov. 8, 2016

(54) METHOD FOR TREATMENT OF BLOOD TUMOR USING ANTI-TIM-3 ANTIBODY

(71) Applicants: KYOWA HAKKO KIRIN CO., LTD, Tokyo (JP); Kyushu University, National University Corporation, Fukuoka (JP)

(72) Inventors: Shinichiro Takayanagi, Tokyo (JP); Yoshimasa Inagaki, Tokyo (JP); Koichi Akashi, Fukuoka (JP); Yoshikane Kikushige, Fukuoka (JP)

(73) Assignees: KYOWA HAKKO KIRIN CO., LTD, Tokyo (JP); Kyushu University, National University Corporation, Fukuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,154

(22) Filed: Jun. 15, 2015

(65) Prior Publication Data

US 2015/0284468 A1    Oct. 8, 2015

Related U.S. Application Data

(60) Continuation of application No. 14/136,394, filed on Dec. 20, 2013, now Pat. No. 9,103,832, which is a division of application No. 13/263,434, filed as application No. PCT/JP2010/056445 on Apr. 9, 2010, now Pat. No. 8,647,623.

(60) Provisional application No. 61/168,428, filed on Apr. 10, 2009.

(51) Int. Cl.
| *A61K 39/395* | (2006.01) |
| *C07K 16/30* | (2006.01) |
| *C07K 16/28* | (2006.01) |
| *G01N 33/574* | (2006.01) |
| *A61K 39/00* | (2006.01) |

(52) U.S. Cl.
CPC ....... *C07K 16/3061* (2013.01); *C07K 16/2803* (2013.01); *G01N 33/57407* (2013.01); *A61K 2039/505* (2013.01); *C07K 2317/73* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| 7,470,428 | B2 | 12/2008 | Kuchroo et al. | |
| 8,552,156 | B2 | 10/2013 | Takayanagi et al. | |
| 8,647,623 | B2 * | 2/2014 | Takayanagi | C07K 16/2803 424/138.1 |

FOREIGN PATENT DOCUMENTS

| JP | 2007530560 A | 11/2007 |
| JP | 2008-500013 A | 1/2008 |
| JP | 2011/518313 A | 6/2011 |
| WO | 9627603 A1 | 9/1996 |
| WO | 03063792 A2 | 8/2003 |
| WO | 2005/033144 A2 | 4/2005 |
| WO | 2005/097211 A2 | 10/2005 |
| WO | 2009-091547 A1 | 7/2009 |

OTHER PUBLICATIONS

Anderson, A. C. et. al. "Promotion of Tissue Inflammation by the Immune Receptor Tim-3 Expressed on Innate Immune Cells", Science, vol. 318, No. 1141, Nov. 16, 2007, pp. 1140-1143.
Bao, S. et. al. "Glioma stem cells promote radioresistance by preferential activation of the DNA damage response", Nature Letters, vol. 444, Dec. 7, 2006, pp. 756-760.
Bernstein, "Monoclonal antibodies to the myeloid stem cells: therapeutic implications of CMA-676, a humanized anti CD33 antibody calicheamicin conjugate", Leukemia, vol. 14, 2000, pp. 474-475.
Bonnet, D. et. al. "Human acute myeloid leukemia is organized as a hierarchy that originates from a primitive hematopoietic cell", Nature Publishing Group, 1997, pp. 730-737.
Christine Vogel et al, "Insights into the regulation of protein abundance from proteomic and transcriptomic analyses", Nature Reviews Genetics, vol. 13, No. 4, Mar. 13, 2012, pp. 227-232, XP055076517.
Communication from the European Patent Office issued Jul. 8, 2014 in a counterpart European Application No. 10761756.5.
European Patent Office, Search Report dated Oct. 28, 2013, issued by the European Patent Office in counterpart European Application No. 10761756.5.
Final Rejection, Issued by the Japan Patent Office, Dated Dec. 9, 2014, in counterpart Japanese Application No. 2011-508396.
Goodell, M. A. et. al. "Isolation and Functional Properties of Murine Hematopoietic Stem Cells that are Replicating In Vivo", J. Exp. Med., Apr. 1, 1996, pp. 1797-1806.
Hafler, D. A. et. al. "TIMs: Central regulators of immune responses" Journal of Experimental Medicine, Nov. 17, 2008, pp. 2699-2701.
Ishikawa, F. et. al. "Chemotherapy-resistant human AML stem cells home to and engraft within the bone-marrow endosteal region", Nature Biology, vol. 25, No. 11, Nov. 2007, pp. 1315-1321.
Japanese Patent Office, Communication dated Apr. 8, 2014, issued in corresponding Japanese Patent Application No. 2011-508396.

(Continued)

*Primary Examiner* — Sheela J Huff
(74) *Attorney, Agent, or Firm* — Sughrue Mion, PLLC

(57) ABSTRACT

Disclosed is a therapeutic method including administering a TIM-3 antibody or its TIM-3 binding fragment to a subject who is suspected to be suffering from blood tumor and in whom TIM-3 has been expressed in a Lin(−)CD34(+)CD38 (−) cell fraction of bone marrow or peripheral blood or a subject who has been received any treatment for blood tumor. Conceived diseases include those diseases which can be treated through the binding or targeting of the TIM-3 antibody or its TIM-3 binding fragment to blood tumor cells (AML cells, CML cells, MDS cells, ALL cells, CLL cells, multiple myeloma cells, etc.), helper T cell (e.g., Th1 cells, Th17 cells), and antigen-presenting cells (e.g., dendritic cells, monocytes, macrophages, and cells resembling to the aforementioned cells (hepatic stellate cells, osteoclasts, microglial cells, intraepidermal macrophages, dust cells (alveolar macrophages), etc)).

18 Claims, 17 Drawing Sheets

(56) References Cited

OTHER PUBLICATIONS

Kikushige, Y. et al. "TIM-3 is a Promising Target to Selectively Kill Acute Myeloid Leukemia Stem Cells", Cell Stem Cell, vol. 7, No. 6, Oct. 6, 2010, pp. 708-717.
Koguchi, K et. al. "Dysregulated T cell expression of TIM3 in multiple sclerosis", The Journal of Experimental Medicine, vol. 203, No. 6, Jun. 5, 2008, pp. 1413-1418.
Majeti, R. et. al. "Dysregulated gene expression networks in human acute myelogenous leukemia stem cells," PNAS, vol. 106, No. 9, Mar. 3, 2009, pp. 3396-3401.
Monney, L. et. al. "Th1-specific cell surface protein Tim-3 regulates macrophage activation and severity of an autoimmune disease", Nature, vol. 415, Jan. 31, 2002, pp. 536-541.
Osakawa, M. et. al. "Long-Term Lymphohematopoietic Reconstruction by a Single CD34-Low/Negative Hematopoietic Stem Cell", Science, vol. 273, Jul. 12, 1996, pp. 242-245.
Yamazaki. S. et. al. "Cytokine signals modulated via lipid rafts mimic niche signals and induce hibernation in hematopoietic stem cells", The EMBO journal, vol. 25, No. 15, 2006, pp. 3515-3523.

\* cited by examiner

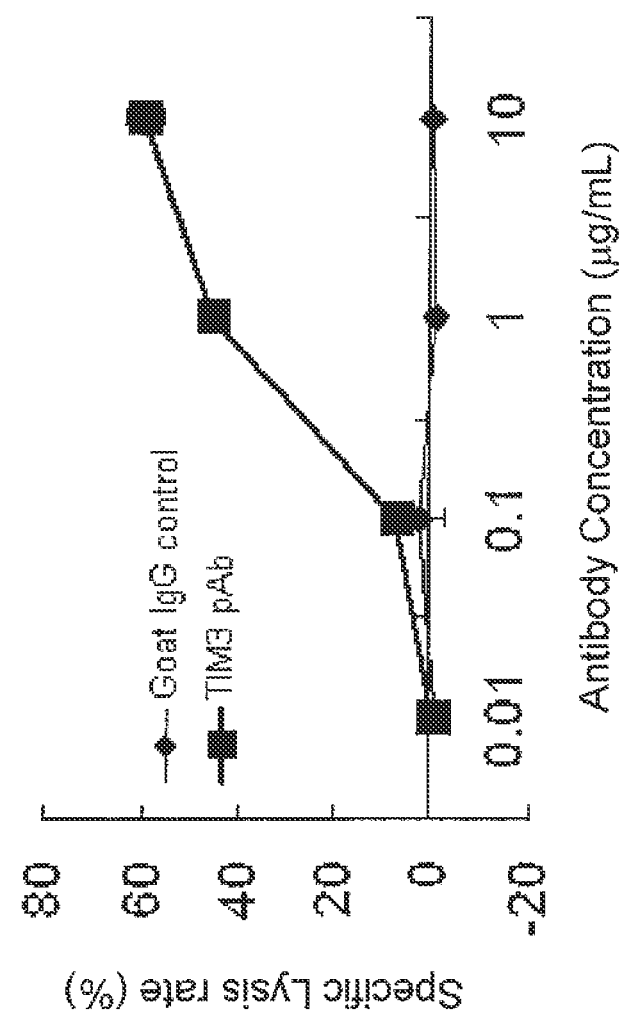

METHOD FOR TREATMENT OF BLOOD TUMOR USING ANTI-TIM-3 ANTIBODY

CROSS REFERENCE TO RELATED APPLICATIONS

This application is a continuation of U.S. application Ser. No. 14/136,394 filed Dec. 20, 2013 (U.S. Pat. No. 9,103, 832), which is a divisional of U.S. application Ser. No. 13/263,434 filed Oct. 7, 2011 (U.S. Pat. No. 8,647,623), which is a National Stage Entry of International Application No. PCT/JP2010/056445 filed Apr. 9, 2010, which claims benefit of U.S. Provisional Application No. 61/168,428 filed Apr. 10, 2009, the contents of all of which are incorporated herein by reference in their entirety.

TECHNICAL FIELD

The present invention relates to an agent for treating or diagnosing myeloid malignancy, especially acute myelogenous leukemia (AML), comprising an antibody to human TIM-3 protein (another name: human HAVCR2) as an active ingredient. In addition, the present invention relates to a method for isolating leukemic stem cells.

BACKGROUND ART

Regarding Malignant Tumor:

A malignant tumor (cancer) is the first leading cause of death in Japan and the number of patients is increasing every year, and the development of a drug and a therapeutic method having high efficacy and safety is strongly desired. Examples of the cause of forming a malignant tumor include a mutation of DNA caused by radiation, ultraviolet rays and various carcinogenic substances. Studies on malignant tumors have been focused on identification of these genetic changes molecular biologically. As a result, it is considered that tumorigenic transformation is induced by accumulation of a large number of mutations and the like. It has been shown by a cell line model and the like that some decisive mutations directly connected with the tumorigenic transformation. Regarding leukemia as one of the objective diseases of the invention, many chromosomal abnormalities have been identified and classified. In many of the case, translocation of chromosome is found and the translocation associated genes have already been identified in the main translocation of chromosome. By functional analyses of the translocation related genes, a case has been found that these genes relates to the onset of leukemia.

Regarding Cancer Stem Cell:

On the other hand, a so-called cancer stem cell hypothesis has been proposed for a long time from the viewpoint of cell biology, stating that stem cell is the origin of a malignant tumor similar to the normal tissue. The stem cell is defined as a cell having self-renewal capacity and pluripotency and generally divided roughly into totipotency stem cell and tissue stem cell. The tissue stem cell is origin of specific tissues and organs such as of blood system, liver, nerve system and the like and present at an extremely low frequency. Among them, the study of hematopoietic stem cell is at the most advanced stage. It has been reported that a hematopoietic system can be reconstituted over a long period of time by transplanting one hematopoietic stem cell into a mouse in which the hematopoietic system was destructed by a lethal dose of irradiation (Non-patent Reference 1). Different from the normal stem cell, studies on cancer stem cells have been delayed for a long time since their true nature could not been found. However, a cancer stem cell has been identified for the first time in acute myelocytic leukemia, in 1997 by Dick et al (Non-patent Reference 2). Thereafter, the presence of cancer stem cells was reported in various malignant tumors. In summing up, cancer stem cells are present at a frequency of several % or less of the whole tumor and the presence of them are rare as well as normal stem cells. It is considered that the remaining cells which form the tumor are tumor precursor cells in which proliferation ability is limited or tumor cells.

From these reports, it was shown that hierarchy is present even in tumor as well as the normal tissue, and the cancer stem cell residing at this top (origin) has strong tumor forming ability. Based on the above, it is considered that the beginning of the onset of malignant tumors is a change from a normal stem cell to a so-called cancer stem cell by addition of several mutations.

Characteristics and Therapeutic Problems of Cancer Stem Cells:

In summing up many reports, it is considered that cancer stem cells are maintaining various characteristics possessed by the normal stem cells. Examples of similarities include rarity of the cell, a microenvironment (niche) in which the stem cells exist, expression of a multiple drug resistance gene, cell cycle, and the like.

Particularly, the characteristics that cancer stem cells express a group of multiple drug resistance genes and are at the stationary phase of cell cycle similar to the normal stem cells could become a therapeutically great problem. A multiple drug resistance gene BCRP is a pump which impairs the drug efficacy by discharging various antitumor agents into outside of cells, and a method for collecting stem cells making use of the activity has been reported (Non-patent Reference 3). In addition, the stem cell is under a state of "hibernation" in order to keep providing cells for its whole life (Non-patent Reference 4) and it reduces in sensitivity for many antitumor agents and radiation (Non-patent References 5 and 6). Based on the above characteristics, it is considered that the rare cancer stem cell which shows resistance to the therapy is a cause of tumor recurrence.

Regarding Molecular Target Drug:

Three main courses of the treatment of a malignant tumor include antitumor agent therapy, radiation therapy and excision. Treatment for the blood tumor is limited to the antitumor agent therapy and radiation therapy, and as described in the above, the cancer stem cell can have a resistance to these treatments. Another problem is that side effects are large since these two treatments affect the entire body. It is a molecular target drug that is expected as a resolving means for this problem. It has a possibility to reduce side effects by exhibiting its drug efficacy only in the cell expressing the target molecule.

Examples of typical drugs of the molecular target drug in the field of blood diseases include imatinib and rituximab. Imatinib targets at a leukemia-causing factor called Bcr-Abl produced by a chromosomal abnormality (Philadelphia chromosome) which is observed in 95% of chronic myeloid leukemia (CML) patients. Imatinib is a low molecular weight drug which induces suicide of leukemia cell by inhibiting function of Bcr-Abl. Rituximab is a therapeutic antibody which recognizes CD20 as a surface molecule on a B cell and has an antitumor effect on non-Hodgkin lymphoma, a malignant tumor of B cell. On the other hand, molecular target drugs for AML are few, and there is only an agent gemtuzumab ozogamicin (Mylotarg) in which an antibiotic calicheamicin is bound to a monoclonal antibody to CD33 known as an AML cell surface antigen (Non-patent Reference 7). However, it can be said that that the use of Mylotarg is limited since Mylotarg can be applied only when a patient meets the following four limitations such as the expression rate of CD33 of 80% or more, a case of recurrency, age of 60 or more, and resistance to other chemical therapy. Based on the above, it can be said that discovery of a new target gene and development of a therapeutic agent for this are important inventions which directly lead to the possibility of therapy and expansion of the choices.

Regarding Embodiment of Molecular Target Drugs:

As the embodiment of molecular target drugs, various substances have been studied and developed such as a therapeutic antibody, a low molecular weight drug, a peptide drug, a biological protein preparation such as cytokine, a siRNA, aptamer and the like. When an antibody is used as a therapeutic agent, due to its specificity, it is useful in treating pathological conditions in which a tumor specific antigen exhibits a property of different cells. The antibody binds to a tumor specific antigen which is a protein expressing on the cell surface and effectively acts upon such cells. The antibody has a characteristic of long blood half life and high specificity for its antigen and is also particularly useful as an antitumor agent. For example, when an antibody targets at a tumor-specific antigen, it can be expected that the administered antibody accumulates into the tumor and thereby attacks the tumor cell via complement-dependent cytotoxicity (CDC) and antibody-dependent cellular cytotoxicity (ADCC) based on the immune system. In addition, by binding a radioactive substance, a cytotoxic substance and the like to an antibody, it becomes possible to transfer an agent efficiently to the tumor part and thereby to allow to act thereon. At the same time, since it can decrease the amount of the reached agent to non-specific other tissues, reduction of side effects can also be expected. Termination or regression of growth of tumor can be expected by activity of antibody accumulated at tumor selectively. Administering antibody will be able to select from antibodies, having agonistic activity when a tumor-specific antigen has an activity to induce cell death, or having neutralization activity when a tumor-specific antigen relates to in the growth and survival of cells. Due to the above characteristics, it is considered that antibodies are suited in applying as antitumor agents.

Regarding Therapeutic Antibodies:

In the original antibody preparation, a mouse was used as the animal to be immunized. However, use of mouse antibodies as drugs in vivo is limited due to a large number of reasons. A mouse antibody which can be recognized as a foreign substance in a human body can induce so-called "human anti-mouse antibody" namely "HAMA" response (Non-patent Reference 8). Further, the Fc region of mouse antibody is not effective for stimulation of human complement or cellular cytotoxicity.

As one of the approaches for avoiding such problems, a chimeric antibody has been developed (EP patent application No. 120694, EP patent application No. 125023). The chimeric antibody contains parts of antibodies derived from two or more species (mouse antibody variable region, human antibody constant region and the like). An advantageous point of such a chimeric antibody is that it keeps the characteristics of a mouse antibody but can stimulate human complement or cellular cytotoxicity since it has human Fc. However, it is known that such a chimeric antibody also induces "human anti-chimeric antibody" namely "HACA" response (Non-patent Reference 9).

Further, it has been developed a recombinant antibody in which only parts of an antibody, complementary determining regions ("CDR"), were substituted (Patent References 1 and 2). By the use of a CDR grafting technique, an antibody comprising mouse CDR and human variable region framework and constant region, so-called "humanized antibody" (Non-patent Reference 10).

Regarding TIM-3:

TIM gene family comprises eight genes in mice and three genes in humans, and these genes are located at chromosome 11 and at gene region 5q33, respectively (Non-patent Document 11). These gene regions are known to relate to autoimmune diseases and allergic diseases. TIM protein is a type I transmembrane protein having a structurally conserved immunoglobulin variable (IgV) domain and a mucin domain. TIM protein was considered to be specifically expressed on T cells and directly regulate the T cell activity, but there are recent reports on expression of TIM-3 protein in antigen-presenting cells and on their functions (Non-patent Document 12). According to the crystal structure analysis, the TIM protein has a conserved protein structure and has a ligand binding site in the IgV domain.

TIM-3 was identified as a molecule specifically expressed on mouse Th1 cells but not on Th2 cells (Non-patent Document 13). In mice, by binding of TIM-3 to its ligand, galectin9, apoptosis is induced in a mouse Th1 cell, the Th1 response is inhibited, and then to lead to induction of peripheral tolerance. In humans, as similar to mice, TIM-3 is selectively expressed on Th1-cells, as well as phagocytic cells such as macrophages and dendritic cells. It is found that the reduction of expression of human TIM-3 by siRNA or inhibition by a blocking antibody increased the secretion of interferon γ (IFN-γ) from CD4 positive T-cells. This supports the inhibitory role of TIM-3 in human T cells. Analysis of clinical samples from autoimmune disease patients showed no expression of TIM-3 in CD4 positive cells. In particular, expression level of TIM-3 is lower and secretion of IFN-γ is higher in T cell clones derived from the cerebrospinal fluid of patients with multiple sclerosis than those in clones derived from normal healthy persons (Non-patent Document 14).

There are reports on relation of TIM-3 with allergic diseases and/or asthma (Patent Documents 3 and 4). However, the relation between TIM-3 and blood cancer is disclosed only in the report on the microarray analysis of hematopoietic stem cell from acute myeloid leukemia patients and normal hematopoietic stem cells (Non-patent Document 15) and many of the relation between TIM-3 and blood cancer has not been found out.

CITATION LIST

Patent Document

Patent Document 1: GB Patent Application No. GB2188638A
Patent Document 2: U.S. Pat. No. 5,585,089
Patent Document 3: WO96/27603
Patent Document 4: WO2003/063792

Non-Patent Document

Non-patent Document 1: Osawa M et al., *Science*. 273:242-5. (1996)
Non-patent Document 2: Bonnet D and Dick J E, *Nat Med*. 3:730-7 (1997)
Non-patent Document 3: Goodell M A et al., *J Exp Med*. 183:1797-806 (1996)

Non-patent Document 4: Yamazaki S et al., *EMBO J.* 25:3515-23 (2006)
Non-patent Document 5: Ishikawa F et al., *Nat Biotechnol.* 25:1315-21. (2007)
Non-patent Document 6: Bao S et al., *Nature.* 444:756-60 (2006)
Non-patent Document 7: Bernstein I D, *Leukemia* (2000) 14, 474-475
Non-patent Document 8: Schiffetal., *Canc. Res.* (1985), 45, 879-885
Non-patent Document 9: Bruggemann, et al., *J. Exp. Med.*, 170, 2153-2157, 1989
Non-patent Document 10: Riechmann, et al., *Nature* (1988), 332, 323-327
Non-patent Document 11: Hafler D A et al., *J Exp Med.* 205:2699-701 (2008)
Non-patent Document 12: Anderson A C et al., *Science* 318:1141-3 (2007)
Non-patent Document 13: Monney L et al., *Nature* 415: 536-41. (2002)
Non-patent Document 14: Koguchi K et al., *J Exp Med.* 203:1413-8. (2006)
Non-patent Document 15: Majeti R et al., *Proc Natl Acad Sci USA.* 2009 Feb. 13. PMID: 19218430

SUMMARY OF THE INVENTION

Technical Problems

As a problem of a conventional treating method for malignant tumor, the following three problems can be mentioned: firstly, side effects affect the entire body due to an antitumor agent, radiation therapy and the like; secondly, the possibility of relapse of the tumor increases due to remaining rare cancer stem cells which exhibit resistance to treatment; and thirdly, there are a few molecular target drug among drugs in the field of blood tumor.

The first object of the present invention is to provide an agent for prevention, diagnosis, or treatment of various blood tumors by developing an antitumor substance which can bind selectively and attack a malignant tumor cell in which TIM-3 is expressed.

The second object of the present invention is to provide use of TIM-3 molecule based on the finding that TIM-3 is expressed in a blood tumor cell.

As described above, there is high expectation for a novel molecular target drug for a blood tumor including leukemia and it is considered that the finding of a novel target molecule and use thereof lead to a development of safe and effective treating methods. Since an antibody originally has recognition specificity, it is useful as a mean for molecular targeting. Therefore, the present inventors made an earnest study on expression of human TIM-3 in blood tumors and preparation of an antibody to human TIM-3 and, as a result, they found use of TIM-3 as a target for treatment.

Solution to Problems

As solutions to the above problem, for the first problem, the present invention provides to use as an agent for treatment targeting a molecule which is highly expressed in a cancer cell as compared to a normal cell. By using such a molecule, the treatment in which drug efficacy on cancer cells becomes large and adverse effects on normal cells becomes small is possible. Besides, the second problem can be solved by using a molecule which is expressed in a cancer stem cell as a target. The third problem can be solved by an agent for treatment which meets above two points since the number of options of treating methods using a molecular target drug increases.

The present invention provides a novel molecular target drug for treating a blood tumor by using a human monoclonal antibody to TIM-3 which is a highly expressed gene in a malignant tumor and thereby attacking a malignant tumor cell including a cancer stem cell.

The present invention can be summarized as follows.

(1) A method for treatment, comprising administering an anti-TIM-3 antibody to a subject who is suspected to have blood tumor in which a cell expressing TIM-3 is recognized in bone marrow or peripheral blood or a subject who has received treatment for blood tumor in which a cell expressing TIM-3 is recognized in bone marrow or peripheral blood.

(2) A composition for preventing or treating blood tumor of a subject in which a cell expressing TIM-3 is recognized in bone marrow or peripheral blood, comprising an anti-TIM-3 antibody as an active ingredient.

(3) A composition for detecting blood tumor in which a cell expressing TIM-3 is recognized in a cell in bone marrow or peripheral blood from a biological sample derived from a subject, comprising an anti-TIM-3 antibody.

(4) The method or composition according to any one of (1) to (3), wherein the cell is a cell fraction selected from the following (a) to (c):
 (a) Lin(−)CD34(+)CD38(−)
 (b) Lin(−)CD34(+)CD38(+)
 (c) Lin(−)CD34(−)

(5) The method or composition according to any one of (1) to (4), wherein the blood tumor is AML.

(6) The method or composition according to any one of (1) to (4), wherein the blood tumor is lymphoma, MDS or CML.

(7) The method or composition according to any one of (1) to (6), wherein the blood tumor is recurrence and/or refractory.

(8) The method or composition according to any one of (1) to (7), wherein the anti-TIM-3 antibody is an anti-TIM-3 monoclonal antibody.

(9) The method or composition according to (8), wherein the anti-TIM-3 monoclonal antibody is an antibody having ADCC activity and/or CDC activity.

Advantageous Effect of the Invention

TIM-3 is known as a gene which controls immune function in a living body. In the present invention, the inventors apply the newly found nature of TIM-3, that is, express in blood tumor, to establish an usage of an agent for treatment or diagnosis and further the gene as a target for isolating a tumor cell by using an antitumor substances (preferably anti-TIM-3 antibody) targeting TIM-3 expressing cells.

Since now, some molecular target drugs have been developed in the field of blood tumor. However, a few of them target a cancer stem cell. For example, AML treating drug, Mylotarg, which targets a CD33 protein is one of them (Bernstein, *Leukemia* (2000) 14, 474-475). However, as described above, it has limitations such as expression level of CD33, recurrence, age, resistance to chemical therapy.

In Examples of the present invention, cytotoxicity of the anti-TIM-3 antibody on TIM3 expressing cells or AML primary cells is found. This activity suggests therapeutic effects on various blood diseases by the anti-TIM-3 antibody.

BRIEF DESCRIPTION OF THE DRAWINGS

FIG. 17 shows a result of CDC assay of AML cell line using anti-TIM-3 polyclonal antibody.

Figure 1:
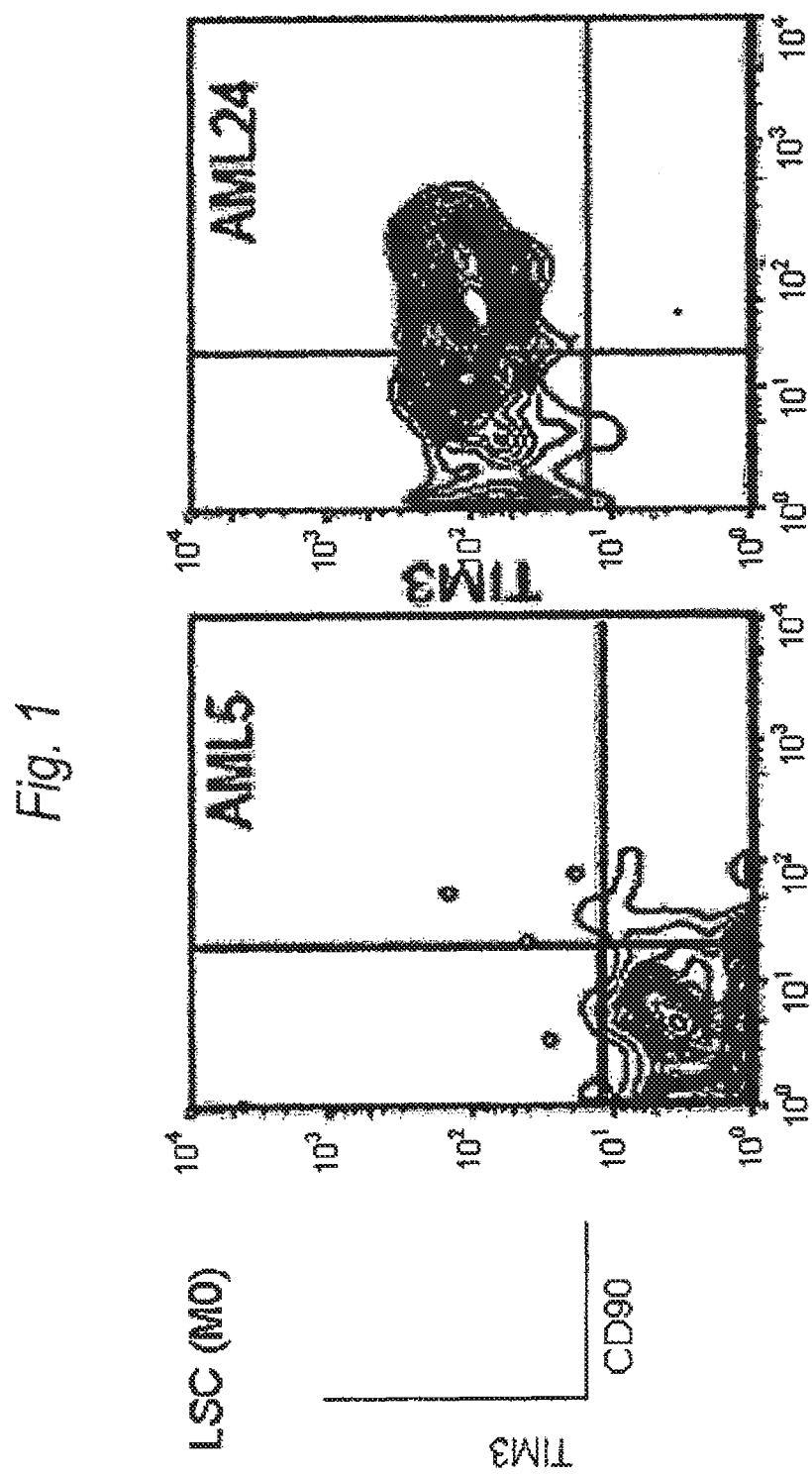
FIG. 1 shows a result of multicolor flow cytometric analysis of expression of human TIM-3 molecule on bone marrow Lin(−)CD34(+)CD38(−) cells derived from an AML (M0) patient.

MODE FOR CARRYING OUT THE INVENTION (Detailed Description of Specified Desirable Embodiments)

Headings of the sections to be used in this specification are only for the purpose of organization and should not be interpreted as limitation to the main subject to be described. All of the cited references cited in this application are clearly incorporated by references into this specification for optional purposes.

(Outline)

This invention provides an agent for prevention, diagnosis or treatment for malignant tumor in which a TIM-3 expressing cell is a target.

In the specific embodiment, the antibody has a binding activity to a TIM-3 molecule and can induce reduction or removal of a TIM-3 expressing cell by an immune system mainly centered on effector cells.

The antibody relates to a functional control of TIM-3 expressing cell and induces survival, growth, resting, cell death or the like.

The antibody relates to a functional control of TIM-3 expressing cell and increases or decreases the amount of production of cytokines or interferon secreted from the cells.

(TIM-3)

TIM gene family consists of eight genes in mouse and three genes in human, and they are located at chromosome 11 and at gene region 5q33. These gene regions are known to be related with autoimmune diseases and allergic diseases. TIM protein is a type I transmembrane protein having a structurally conserved immunoglobulin variable (IgV) domain and a mucin domain.

In addition, a known ligand of TIM-3, galectin-9, is reported to express on peripheral leukocytes and lymphoid tissue in human (Wada J et al., J Biol Chem. 272: 6078-86 (1997)). It is known that human galectin-9 binds to GLUT-2 transporter protein and various oligosaccharide other than TIM-3 (Nagae M et al., J Mol Biol. 375: 119-35 (2008)).

In addition, TIM-3 is also called as HAVCR2. TIM-3 includes mammal (such as primate and human) TIM-3. Therefore, the anti-TIM-3 antibody of the present invention includes an antibody which specifically binds to the sequence of mammal TIM-3 such as human TIM-3. The sequence of TIM-3 such as human TIM-3 includes polymorphic variants. A non-specific example of the full length human TIM-3 includes the sequence described as follows:

```
                                        (SEQ ID NO: 1)
MFSHLPFDCVLLLLLLLLTRSSEVEYRAEVGQNAYLPCFYTPAAPGNLV

PVCWGKGACPVFECGNVVLRTDERDVNYWTSRYWLNGDFRKGDVSLTIE

NVTLADSGIYCCRIQIPGIMNDEKFNLKLVIKPAKVTPAPTRQRDFTAA

FPRMLTTRGHGPAETQTLGSLPDINLTQISTLANELRDSRLANDLRDSG

ATIRIGIYIGAGICAGLALALIFGALIFKWYSHSKEKIQNLSLISLANL

PPSGLANAVAEGIRSEENIYTIEENVYEVEEPNEYYCYVSSRQQPSQPL

GCRFAMP
```

(Antibody)

The antibody is used in a most broad sense and includes a monoclonal antibody, a polyclonal antibody, a multivalent antibody, a multispecific antibody (e.g., bispecific antibody) and also antibody fragments as long as these exhibit the desired biological activity.

The antibody contains a mature heavy chain or light chain variable region sequence. In addition, the antibody also includes a modified form and variant form such as substitutions within or outside of a constant region, a complementary determining region (CDR) or a framework (FR) region of a mature heavy or light chain variable region sequence of the antibody, and the like. In a specific embodiment, the substitution includes a conservative amino acid substitution is included in the substitution.

In addition, the antibody also includes a subsequence of the mature heavy chain or light chain variable region sequence. In a specific embodiment, the subsequence is selected from Fab, Fab', F(ab')$_2$, Fv, Fd, single chain Fv (scFv), disulfide bond Fv (sdFv) and VL or VH.

In addition, the antibody also includes a heterogeneous domain. In a specific embodiment, the heterogeneous domain includes a tag, a detectable label or a cytotoxic agent.

Examples of the antibody include a monoclonal antibody and a polyclonal antibody and any isotype or subclass thereof. In a specific embodiment, the aforementioned antibody is an isotype of IgG (e.g., IgG1, IgG2, IgG3 or IgG4), IgA, IgM, IgE or IgD. The "monoclonal" antibody means an antibody that is based upon a single clone including a eukaryote clone, a prokaryote clone or a phage clone, obtained from a single clone including a eukaryote clone, a prokaryote clone or a phage clone, or induced from a single clone including a eukaryote clone, a prokaryote clone or a phage clone. Accordingly, the "monoclonal" antibody is a structurally defined substance and not a method by which it is produced.

The TIM-3 antibody, anti-TIM-3 and anti-TIM-3 antibody mean an antibody which specifically binds to TIM-3. The specific binding means that it is selective for the epitome presenting in TIM-3. The specific binding can be distinguished from non-specific binding using a known assay in the technical field (e.g., immunoprecipitation, ELISA, flow cytometry, and Western blotting).

When all or a part of antigen epitopes to which an anti-TIM-3 antibody specifically binds are present in different proteins, there is a possibility that this antibody can bind to the different proteins. Therefore, there is a possibility that the TIM-3 antibody specifically binds to other protein having high sequence or structural homology to TIM-3 epitope depending on the sequence or structural homology of TIM-3 epitope. Accordingly, there is a possibility that TIM-3 antibody binds to a different protein when an epitope having sufficient sequence or structural homology is present in the different protein.

The TIM-3 antibody includes isolated and purified antibodies. The antibody of the invention including an isolated or purified TIM-3 antibody includes human.

The term "(be) isolated" to be used as a modifier of a composition means that the composition is prepared by the hand of man or separated from one or more other components in in vivo environment presenting in nature generally by one or more manipulative steps or processes. In general, a composition separated in this manner does not substantially contain one or more materials with which they normally associate in nature, such as one or more proteins, nucleic acids, lipids, carbohydrates and cell membranes. Because of this, the isolated composition is separated from other biological components in the cells of the organism in which the composition naturally occurs, or from the artificial medium in which it is produced (e.g., by synthesis or cell culture). For example, an isolated TIM-3 antibody can be obtained from an animal in which the antibody is produced (e.g., non-transgenic mammals or transgenic mammals (such as rodents (mouse), the ungulates (cattle) and the like)) and is separated from other polypeptides and nucleic acids. Accordingly, it is considered that the serum containing an antibody obtained from such an animal is isolated. The term "(be) isolated" does not exclude alternative physical forms, and for example, an isolated antibody could include antibody subsequences, chimerized, multimerized or derivatized forms.

The term "(be) purified" to be used as a modifier of a composition refers to a composition which is free of most of or substantially all of the materials with which it typically associates in nature. In general, a purified antibody is obtained from the components generally presenting in the antibody environment. Because of this, it is considered that an antibody supernatant which is separated from a cell culture mixture of an antibody producing hybridoma is purified. Accordingly, the "(be) purified" does not require absolute purity and is context specific. Furthermore, the "(be) purified" composition can be combined with one or more other molecules. Because of this, the term "(be) purified" does not exclude combination of composition. The purity can be determined by an optional appropriate method such as UV spectrometry, chromatography (e.g., HPLC, gas phase), gel electrophoresis (e.g., silver or Coomassie staining), sequence analysis (peptide and nucleic acid) and the like.

The "(be) purified" protein and nucleic acid include a protein and a nucleic acid which are obtained by a standard purification method. Also, a protein and a nucleic acid obtained by recombination expression in a host cell and chemical synthesis are also included in this term. In addition, the "(be) purified" can also refer to a composition in which the level of contaminants is lower than the level which is acceptable to a regulatory agency for administration to human or non-human animals, such as the Food and Drug Administration (FDA).

The anti-TIM-3 antibody also includes one which can specifically bind to TIM-3 expressed on the cell. In specific embodiment, the anti-TIM-3 antibody can specifically bind to TIM-3 expressing blood tumor cells (AML cells, CML cells, myelodysplastic syndromes (MDS) cells, ALL cells, CLL cells, Multiple Myeloma cells, or various lymphoma such as B-cell lymphoma, T cell lymphoma, NK-cell lymphoma), helper T cell (e.g., Th1 cell, Th17 cell), an antigen-presenting cells (such as dendritic cells, monocytes, macrophage and subtypes thereof (e.g., hepatic stellate cell, osteoclast, microglia, intraepidermal macrophage, dust cell (alveolar phagocyte))) or TIM-3 expressed in a TIM-3 gene transfected cell.

Examples of the anti-TIM-3 antibody include an antibody which specifically binds to an epitope in the amino acid sequence of extracellular region of TIM-3. In the specific embodiments, exemplary anti-TIM-3 antibody specifically binds to three epitopes on TIM-3 as decided by across-blocking assay. A non specific exemplary sequence of the human TIM-3 extracellular region is as follows.

```
                                              (SEQ ID NO: 2)
MFSHLPFDCVLLLLLLLLLTRSSEVEYRAEVGQNAYLPCFYTPAAPGNLV

PVCWGKGACPVFECGNVVLRTDERDVNYWTSRYWLNGDFRKGDVSLTIE

NVTLADSGIYCCRIQIPGIMNDEKFNLKLVIKPAKVTPAPTRQRDFTAA

FPRMLTTRGHGPAETQTLGSLPDINLTQISTLANELRDSRLANDLRDSG

ATIR
```

Examples of the anti-TIM-3 antibody include an antibody which can bind to TIM-3 existing on one or more kinds of the cells in vivo, isolated primary cultured cells, subcultured cells, cultured cells and immortalized cells. Specific examples of non-specific cell types which can express TIM-3 include AML cells, other blood tumor cells (such as CML cells, ALL cells, CLL cells, MDS cells, Multiple Myeloma cells, various lymphoma cells (e.g., B-cell lymphomas, T cell lymphoma, NK cell lymphoma and the like)) and non-blood tumor cells. Examples of non-blood tumor cells include monocytes, dendritic cells, macrophages, helper T cells, natural killer cells, myeloid progenitor cells and lymphoid progenitor cells. TIM-3 can be expressed in a cell which originally does not express TIM-3 by transfection or transformation using the nucleic acid encoding TIM-3. The anti-TIM-3 antibody which can bind TIM-3 can bind one or more transfectant or transformant expressing or producing TIM-3.

In the present specification, AML cells, CML cells, ALL cells, CLL cells, MDS cells, Multiple Myeloma cells, various lymphoma cells, such as B-cell lymphomas, T cell lymphoma, NK cell lymphoma, include their cancer stem cells.

The cancer stem cell is one of the population of cell constituting tumor and it is represented by Lineage(−)CD34(+)CD38(−) myeloid cell. As another name corresponding to disease, a tumor stem cell, a leukemia stem cell and the like are known.

Among the blood tumor cells, leukemia cells obtained from bone marrow of a patient of leukemia (such as leukemia stem cells and blast cells) can be fractionated according to a differentiation antigen (Lineage marker) and a cell surface marker such as CD34 and CD38. Most of leukemia stem cells reside in the Lineage(−)CD34(+)CD38(−) cell fraction. On the other hand, the blast cell is identified morphologically. Although it is a Lineage(−)CD34(+)CD38(+) cell, it also exists in various cell groups including Lineage(−)CD34(+)CD38(−) cell fraction and Lineage(−)CD34(−)cell fraction.

The TIM-3 antibody includes an antibody which binds to TIM-3 and modulates function or activity of TIM-3 in vivo or in vitro (e.g., in a subject). In the specification, the "to modulate" and the grammatical variations thereof when used in relation to the activity or function of TIM-3 mean that the TIM-3 activity or function is detectably affected, modified or altered. Accordingly, the TIM-3 antibody which modulates the activity or function of TIM-3 is an antibody that provides influence, modification or alteration such that one or more of the TIM-3 activity or function can be detected, and such an activity or function of TIM-3 can includes, for example, binding of TIM-3 with an TIM-3 ligand, an TIM-3-mediated signal transduction or an TIM-3-mediated cell response or a cell response that can be modulated by TIM-3, or the activity or function of other TIM-3 described in the specification or, otherwise, is commonly known or can be known.

Examples of various non-limited TIM-3 activities and functions which can be modulated include TIM-3 mediated signal transduction or TIM-3 mediated cellular response, cellular response which can be modulated via TIM-3, cell proliferation or cell expansion (e.g., AML cells, CML cells, ALL cells, CLL cells, MDS cells, Multiple Myeloma cells, various lymphoma cells, such as B-cell lymphomas, T cell lymphoma, and NK cell lymphoma, monocytes, dendritic cells, macrophages, helper T cells, natural killer cells, myeloid progenitor cells and lymphoid progenitor cells), cell survival or cell death such as apoptosis (e.g., AML cells, CML cells, ALL cells, CLL cells, MDS cells, Multiple Myeloma cells, various lymphoma cells, such as B-cell lymphomas, T cell lymphoma, and NK cell lymphoma, monocytes, macrophages, helper T cells, natural killer cells, myeloid progenitor cells and lymphoid progenitor cells), cytokines (e.g., Th1, Th2 and non-Th1/Th2 cytokines) and expression or production of interferon, expression or production of anti-apoptosis protein or proapoptosis protein, treatment, suppression or improvement of disorder, disease, physiological condition, pathological condition and symptom of them. Specific cytokines to be modulated are not limited and examples include IL-1, IL-2, IL-4, IL-5, IL-6, IL-9, IL-10, IL-14, IL-16, IL-17, IL-23, IL-26, TNF-α, and interferon γ (in vitro or in vivo). Specific anti-apoptosis proteins and proapoptosis proteins are not limited and examples include Bcl-xL, Bcl-2, Bad, Bim, and Mcl-1.

Therefore, examples of anti-TIM-3 antibody described in the present specification include an antibody which modulates TIM-3 mediated one or more signal transduction or TIM-3 mediated cellular response, cellular response which can be induced by TIM-3, cell proliferation (e.g., AML cells, CML cells, ALL cells, CLL cells, MDS cells, Multiple Myeloma cells, various lymphoma cells such as B-cell lymphomas, T cell lymphoma, and NK cell lymphoma, monocytes, macrophages, helper T cells, natural killer cells, myeloid progenitor cells and lymphoid progenitor cells), cell survival or apoptosis (e.g., AML cells, CML cells, ALL cells, CLL cells, MDS cells, Multiple Myeloma cells, various lymphoma cells such as B-cell lymphomas, T cell lymphoma, and NK cell lymphoma, monocytes, macrophages, helper T cells, natural killer cells, myeloid progenitor cells and lymphoid progenitor cells), expression or production of cytokines (e.g., Th1, Th2 and non-Th1/Th2 cytokines, IL-17, IL-23 and IL-26) and interferon (e.g., Th1, Th2, non-Th1/Th2, IL-1, IL-2, IL-4, IL-5, IL-6, IL-9, IL-10, IL-14, IL-16, IL-17, IL-23, IL-26, TNF-α, interferon γ, and GM-CSF (in vivo or in vitro) and the like), expression of anti-apoptosis protein or proapoptosis protein (e.g., Bcl-xL, Bcl-2, Bad, Bim and Mcl-1), treatment, suppression or improvement of disorder, disease, physiological condition, pathological condition and symptom. In the specific embodiments, anti-TIM-3 antibody of the present invention can modulate expansion or survival of AML cell, number of other blood tumor cell (e.g., CML cells, ALL cells, CLL cells, MDS cells, Multiple Myeloma cells, or various lymphoma cells such as B-cell lymphomas, T cell lymphoma, and NK cell lymphoma), growth or survival of non-blood tumor cell such as monocytes, dendritic cells, macrophages, helper T cells, natural killer cells, myeloid progenitor cells and lymphoid progenitor cells, and reduces, disappears or depletes AML cells, CML cells, ALL cells, CLL cells, MDS cells, Multiple Myeloma cells, and various lymphoma cells, such as B-cell lymphomas, T cell lymphoma, and NK cell lymphoma.

The TIM-3 antibody includes a modified form such as a substitution product (e.g., an amino acid substitution product) which is also called as "variant", an addition product, deletion product (e.g., a subsequence or fragment) and the like. Such modified antibody forms and variants retain at least partial function or activity of the TIM-3 antibody shown by the invention, such as binding with TIM-3, or modulation of activity or function (e.g., TIM-3 signal transduction) of TIM-3. Accordingly, the modified TIM-3 antibody can retain the ability to modulate, for example, at least partial of TIM-3 binding or one or more of the TIM-3 functions or activities (e.g., signal transduction, cell response and the like).

According to this specification, the term "to alter" ("to modify") and the grammatical variations thereof means that the composition derivarates a reference composition. The altered proteins, nucleic acids and other compositions can have higher or lower activities than a reference unmodified protein, nucleic acid or other composition or can have a different function from a reference unmodified protein, nucleic acid or other composition.

Such an antibody containing an amino acid substitution can be encoded by nucleic acid. Accordingly, the present invention also provides a nucleotide sequence encoding an antibody containing an amino acid substitution.

The term "identity" or "identical" means that two or more referenced substances are the same. Accordingly, when two protein sequences (e.g., TIM-3 antibodies) are identical, they have the same amino acid sequences at least within the referenced regions or portion. The term "identical region" means an identical region of two or more referenced substances. Thus, when two protein sequences are identical over one or more sequence regions, they have identity within the regions. "Substantial identity" means that a molecule is structurally or functionally conserved such that the molecule has or is predicted to have at least partial function or activity of one or more of reference molecule functions or activities or relevant/corresponding region or a portion of the reference molecule to which it shares identity. Thus, polypeptides having substantial identity (e.g., TIM-3 antibodies) have or are predicted to have at least a part of the activity or function as a referenced polypeptide (e.g., TIM-3 antibody). For example, in a specific embodiment, it is considered that a TIM-3 antibody having one or more modifications (e.g., amino acid substitution, deletion or addition) which retain at least partial activity or function of the unmodified TIM-3 antibody has substantial identity to the reference TIM-3 antibody.

Due to variations between structurally related protein and functionally related protein, the amount of sequence identity may vary with what is required to retain functions of the protein, activity of the protein, function of the region, or activity of the region. In the case of protein, an activity or function can be retained by the presence of merely 30% of amino acid sequence identity, but in general, higher identity of 50%, 60%, 75%, 85%, 90%, 95%, 96%, 97% or 98%, to the reference sequence is present. The extent of identity between two sequences can be confirmed using a computer program or mathematic algorithm conventionally known in the technical field. In such an algorithm which calculates ratio of sequence identity (homology), in general, sequence gaps and mismatches over the comparison region are accounted. For example, BLAST (e.g., BLAST 2.0) retrieval algorithm (e.g., see Altschul et al., *J. Mol. Biol.*, 215: 403 (1990), publicly available through NCBI) has the following illustrative retrieval parameters: mismatch −2; gap start 5; gap elongation 2. In the polypeptide sequence comparison, the BLASTP algorithm is typically used in combination with a scoring matrix such as PAM 100, PAM 250, BLOSUM 62, BLOSUM50.FASTA (e.g., FASTA 2 and FASTA 3) and the like, and SSEARCH sequence comparison program is also used for determining the extent of identity (Pearson et al., *Proc. Natl. Acad. Sci. USA*, 85: 2444 (1988); Pearson, *Methods Mol. Bio.*, 132: 185 (2000); and Smith et al., *J. Mol. Biol.*, 147: 195 (1981)). A program has also been developed for determining protein structural similarity using topological mapping based on Delaunary (Bostick et al., *Biochem. Biophys. Res. Commun.*, 304: 320 (2003)).

A "conservative substitution" is a substitution of one amino acid by a biologically, chemically or structurally similar residue. Biological similarity means that a biological activity such as TIM-3 binding activity is not destroyed by the substitution. Structural similarity means that amino acids have side chain with similar length (e.g., alanine, glycine and serine) or have similar size. Chemical similarity means that the residues have the same charge or are both hydrophilic or hydrophobic. Specific examples include substitution of one hydrophobic residue such as isoleucine, valine, leucine, and methionine with other residue, or the substitution of one polar residue with other residue such as the substitution of arginine with lysine, the substitution of glutamic acid with aspartic acid, or the substitution of glutamine with asparagine, and the substitution of serine with threonine.

In addition, examples of the modified antibody include peptide mimetics having one or more D-amino acids substituted with L-amino acids (and a mixture thereof), structural and functional analogs such as synthesized or non-natural amino acids or amino acid analogs, and derivatized form thereof. Examples of modification include a cyclic structure such as an end-to-end amide bond between the amino and carboxy-terminus of the molecule or intra- or inter-molecular disulfide bond.

Additional specific non-limiting examples of the amino acid modifications include partial sequence (subsequence) and fragment of TIM-3. Exemplary subsequence and fragment of TIM-3 include a part of the TIM-3 sequence to which the exemplary TIM-3 antibody of the invention binds. Also, the exemplary subsequence and fragment of TIM-3 include an immunogenicity region such as a part of the TIM-3 to which the exemplary TIM-3 antibody of the invention binds.

The TIM-3 antibody subsequence and fragment can have a binding affinity as the full length antibody, a binding specificity as the full length antibody or one or more activities or functions as the full length antibody, such as the function or activity of an TIM-3 antagonist or agonist antibody. The terms "functional subsequence" and "functional fragment" in the case of referring to the antibody mean an antibody portion which retains one or more functions or activities as the full length reference antibody, such as at least a part of the function or activity of TIM-3 antibody. For example, an antibody subsequence which binds to TIM-3 or a fragment of TIM-3 is considered a functional subsequence.

The antibody subsequence and fragment can be combined. For example, a VL or VH subsequence can be connected by a linker sequence and thereby can form a VL-VH chimeric body. A combination of single chain Fv (scFv) subsequences can be connected by a linker sequence and thereby can form a scFv-scFv-chimeric body. The TIM-3 antibody subsequence and fragment include a single chain antibody or variable region alone or in combination with all or a portion of other TIM-3 antibody subsequence.

The antibody subsequence and fragment can be prepared by hydrolysis of the antibody by its proteolysis for example by a pepsin or papain digestion of the whole antibody. The antibody subsequence and fragment obtained by enzymatic cleavage with pepsin provide a 5S fragment represented by F(ab')$_2$. This fragment can be further cleaved using a thiol reducing agent to form a 3.5S Fab' monovalent fragment. Alternatively, an enzymatic cleavage using pepsin directly produces two monovalent Fab' fragments and Fc fragment (see e.g., U.S. Pat. Nos. 4,036,945 and 4,331,647; and Edelman et al., *Methods Enzymol.*, 1: 422 (1967)). Other methods of cleaving an antibody, such as separation of heavy chain for forming a monovalent light chain-heavy chain fragment, further cleavage of the fragment or other enzymatic or chemical method may be used.

A protein and an antibody, as well as subsequence thereof and fragment can be prepared using a genetic method. The technology includes the full or partial gene encoding a protein or an antibody is expressed in a host cell such as a COS cell and *E. Coli*. A recombinant host cell synthesizes the full or subsequence such as scFv (such as Whitlow et al, In: Methods: A Companion to Methods in Enzymology 2:97 (1991), Bird et al, *Science* 242:423 (1988); and U.S. Pat. No. 4,946,778). A single chain Fv and an antibody can be prepared in accordance with the procedure as described in U.S. Pat. Nos. 4,946,778 and 5,258,498; Huston et al, Methods Enzymol 203:46 (1991); Shu et al, *Proc. Natl. Acad. Sci. USA* 90:7995 (1993); and Skerra et al, *Science* 240:1038 (1988).

The modified form includes a derivatized sequence such as amino acids in which the free amino groups form amine hydrochloride, p-toluenesulfonyl group and carbobenzoxy group; the free carboxy groups which form a salt or methyl and ethyl ester; and the free hydroxyl groups form O-acyl or O-alkyl derivatives, and naturally existing amino acid derivatives such as 4-hydroxyproline (derivative of proline), 5-hydroxylysine (derivative of lysine), homoserine (derivative of serine), ornithine (derivative of lysine) and the like. The modification can be carried out using a method conventionally known in the technical field (e.g., site-specific deletion or insertion mutagenesis based on PCR, chemical modification and mutagenesis, crosslinking and the like).

Addition products and insertion products are included in the modified forms of protein (e.g., antibody), nucleic acid and other compositions. For example, the addition can be a covalent or non-covalent bond with any type of molecules of protein (e.g., antibody), nucleic acid or other compositions. In general, addition and insertion confer different function or activity.

Fusion (chimeric) polypeptides or nucleic acid sequences are included in the addition product and insertion product, and these are sequences having one or more molecules which are generally not present in the reference native (wild type) sequence covalently attached to the aforementioned sequence. A specific example is an amino acid sequence of other protein (e.g., an antibody) for producing a multifunctional protein (e.g., a multispecific antibody).

Also, the antibody of the invention include a chimeric or fusion product in which one or more additional domains are covalently linked thereto in order to impair a different or complementary function or activity. Examples of the antibody include a chimeric or fusion product which does not naturally present in natural and in which two or more amino acid sequences are mutually bonded.

A linker sequence may be inserted between the protein (e.g., an antibody), nucleic acid or other composition and the addition product or insertion product (e.g., a heterologous domain) so that the two substances maintain at least a part of different function or activity. The linker sequence may have one or more properties which can accelerate either of the domains or can carry out mutual reaction with either of the domains, and such characteristics include impossibility to form a flexible structure and an ordered secondary structure or hydrophobic property or charging property. Examples of the amino acids which are generally found in the flexible protein regions include glycine, asparagine and serine. Other amino acids close to neutral such as threonine and alanine may also be used in the linker sequence. The length of the linker sequence can be varied (e.g., see U.S. Pat. No. 6,087,329). The linker further include chemical crosslinking agents and binding agents (conjugating agents) such as a sulfo-succinimidyl derivative (sulfo-SMCG, sulfo-SMPB), disuccinimidyl suberate (DSS), disuccinimidyl glutarate (DSG) and disuccinimidyl tartarate (DST).

Further examples of the addition include any one of glycosylation, fatty acid, lipid, acetylation, phosphorylation, amidation, formylation, ubiquitination and derivatiation by a protecting or blocking group and a large number of chemical modifications. Other substitutions and possibilities can be easily understood by those skilled in the art and are considered to be within the scope of the invention.

Such a modified sequence can be prepared using recombinant DNA techniques which mediate cell expression or in vitro translation. Polypeptides and nucleic acid sequences can also be prepared by a conventionally known method in the technical field such as chemical synthesis using an automatic peptide synthesizer (see e.g., Applied Biosystems, Foster City Calif.).

Modified and variant antibodies such as substitution products, subsequences addition products and the like can maintain detectable activity of TIM-3 antibody. In an embodiment, the modified antibody has the activity to bind to TIM-3 molecule and induces reduction or elimination of TIM-3 expression cells by an immune system mainly centering on an effector cell. The modified antibody relates to the functional control of TIM-3 expression cells and induces survival, growth, resting, cell death and the like of the cells. The cell death includes apoptosis, necrosis, autophagy and the like.

According to the invention, there are further provided a cell-free method (e.g., in a solution or by a solid phase) and a cell-based method (e.g., in vivo or in vitro) which screen, detect and identify TIM-3. These methods can be carried out in a solution in vitro using a biomaterial or sample, and in vivo for example using a sample of an animal-derived cell (e.g., lymphocyte). In an embodiment, the method comprises a step of contacting a biomaterial or sample with a TIM-3-binding antibody under a condition of allowing binding of the antibody to TIM-3 and a step of assaying for binding of the antibody to TIM-3. The presence of TIM-3 is detected by binding of the antibody to bind to TIM-3. In an embodiment, TIM-3 is present in a cell or tissue. In another embodiment, the aforementioned biomaterial or sample is obtained from a mammal analyte.

The term "contacting" when it is used in relation to the composition such a protein (e.g., TIM-3 antibody), a material, a sample or treatment means a direct or indirect interaction between the composition (e.g., TIM-3 antibody) and other referenced substance. Specific examples of the direct interaction include bonding. Examples of specific examples of the indirect interaction include a case in which the composition acts upon an intermediate molecule and this intermediate molecule then acts upon the referenced substance. Accordingly, for example, contacting a cell (e.g., lymphocyte) to TIM-3 antibody includes the antibody to bind to the cell (e.g., through binding to TIM-3) or to allow the antibody to act on an intermediate substance, followed by the action of this intermediate substance upon the cell.

The terms "assaying" and "measuring" and grammatical variations thereof are synonymously used in the specification and mean either of qualitative measurement and quantitative measurement or both of qualitative measurement and quantitative measurement. When these terms are used in relation to binding, they include any means of evaluating relative amount, affinity or specificity of binding including various methods which are described in the specification and conventionally known in the technical field. For example, binding of the TIM-3 antibody with TIM-3 can be assayed or measured by a flow cytometry assay.

(Preparation of Antibody)

The invention also provides a method for preparing a human TIM-3 antibody having TIM-3-positive cytotoxicity. In an embodiment, the method comprises administering a human TIM-3 extracellular region conjugated with a human Fc recombinant protein or an TIM-3 gene introduced cell to animals capable of expressing human immunoglobulin (e.g., transgenic mice or transgenic cattle); screening the animal for expression of a anti-human TIM-3 antibody; selecting an animal producing the anti-human TIM-3 antibody; isolating the antibody from the selected animal and deciding whether or not anti-human TIM-3 antibody has TIM-3 antagonistic activity.

The TIM-3 protein suitable for the antibody preparation can be produced by any one of various standard protein purification and recombinant expression techniques. For example, the TIM-3 sequence can be prepared by standard peptide synthesis techniques such as a solid phase synthesis. In order to facilitate purification of the expressed or synthesized protein, a portion of the protein may contain an amino acid sequence such as a FLAG tag, a T7 tag, a polyhistidine sequence or the like. The protein is expressed inside the cells and can be purified. The protein can be expressed by a recombination method as a part of a further large protein (e.g., a fusion or chimeric product). The embodiment of the TIM-3 suitable for generating immune response includes TIM-3 subsequences such as an immunogenicity fragment. Further embodiment of TIM-3 includes a TIM-3 expressing cell, a TIM-3 containing preparation or cell extract or fraction and a partially purified TIM-3.

The method for preparing polyclonal antibody and monoclonal antibody is conventionally known in the technical field. For example, TIM-3 or its immunogenicity fragment used for immunizing an animal by optionally conjugating with a carrier such as keyhole limpet hemocyanin (KLH) or ovalbumin (e.g., BSA) or mixing with an adjuvant such as complete or incomplete Freund's adjuvant. By isolating a spleen cell derived from an immunized animal which responds to TIM-3, it can be fused with myeloma cell using hybridoma techniques. The monoclonal antibodies produced by hybridomas can be screened for reactivity with TIM-3 or immunogenicity fragment thereof.

The animal which can be immunized includes the primates, mouse, rat, rabbit, goat, sheep, cattle and guinea pig. The initial and any optionally subsequent immunization may be by intravenous route, intraperitoneal route, intramuscular route or subcutaneous route. Further, in order to increase immune response, the antigen can be conjugated with other protein such as ovalbumin, keyhole limpet hemocyanin (KLH), thyroglobulin and tetanus toxoid, or can be mixed with an adjuvant such as complete Freund's adjuvant, incomplete Freund's adjuvant and the like. The initial and any optionally subsequence immunization may be through intraperitoneal route, intramuscular route, intraocular route or subcutaneous route. The immunization may be at the same concentration or different concentration of a TIM-3 preparation, and at regular or irregular intervals.

The animal includes those which are genetically modified to include human loci, and a human antibody can be prepared using the same. Examples of the transgenic animals with one or more human immunoglobulin genes, are described for example in U.S. Pat. No. 5,939,598, WO02/43478 and WO02/092812. Using conventional hybridoma technique, a spleen cells which is isolated from immunized mouse having high responders to the antigen and fuse it with myeloma cell. A monoclonal antibody which binds to TIM-3 can be obtained.

The method for producing a human polyclonal antibody and a human monoclonal antibody is further described (see, such as Kuroiwa et al, *Nat. Biotechnol.* 20: 889 (2002); WO98/24893; WO92/01047; WO96/34096; WO96/33735; U.S. Pat. Nos. 5,413,923; 5,625,126; 5,633,425; 5,569,825; 5,661,016; 5,545,806; 5,814,318; 5,885,793; 5,916,771; and 5,939,598).

The term "human" when it is used in reference to an antibody means that amino acid sequence of the antibody is completely the human amino acid sequence, namely is human heavy chain and human light chain variable regions and human constant region. Accordingly, all of the amino acids are human amino acids or present in the human antibody. An antibody which is a non-human antibody can be made into a complete human antibody by substituting the non-human amino acid residues with the amino acid residues which are present in the human antibody. The amino acid residues which are present in the human antibody, CDR region map and human antibody consensus residues are well known in the technical field (see e.g., Kabat, *Sequences of Proteins of Immunological Interest*, 4th edition, US Department of Health and Human Services, Public Health Service (1987); Chothia and Lesk (1987)). A consensus sequence of human VH subgroup III based on the investigation carried out using 22 known human VH III sequences as the object and a consensus sequence of human VL κ chain subgroup I based on the investigation carried out using 30 known human κ chain I sequences as the object are described in Padlan, *Mol. Immunol.*, 31: 169 (1994) and Padlan, *Mol. Immunol.*, 28: 489 (1991). Accordingly, the human antibody includes an antibody in which one or more amino acid residues have been substituted with one or more amino acids existing in an optional other human antibody.

Examples of the anti-TIM-3 antibody include antibodies prepared using a known method in the technical field, such as CDR-grafting (EP 239,400; WO91/09967; U.S. Pat. Nos. 5,225,539; 5,530,101; and 5,585,089), veneering or resurfacing (EP592,106; EP519,596; Padlan, Molecular Immunol. 28: 489 (1991); Studnicka et al., Protein Engineering 7: 805 (1994); Roguska et al., *Proc. Nat'l Acad. Sci. USA* 91: 969 (1994)) and chain shuffling (U.S. Pat. No. 5,565,332). In order to produce a humanized antibody, human consensus sequence (Padlan, *Mol. Immunol.* 31:169 (1994); and Padlan, *Mol. Immunol.* 28: 489 (1991)) has been used (Carter et al., *Proc. Natl. Acad. Sci. USA* 89: 4285 (1992); and Presta et al, *J. Immunol.* 151: 2623 (1993)).

The term "humanized" when it is used in relation to an antibody means that amino acid sequence of the antibody has one or more non-human amino acid residues (e.g., mouse, rat, goat, rabbit and the like) of complement determining region (CDR) which specifically binds to a desired antigen in an acceptor human immunoglobulin molecule and one or more human amino acid residues (amino acid residues which are flanked with CDR) in Fv framework region (FR). The antibody called "primatized" is within the scope of meaning of "humanized", except that amino acid residues of the acceptor human immunoglobulin molecule and framework region can be any primate amino acid residues (e.g., monkey, gibbon, gorilla, chimpanzee, orangutan, macaque monkey) in addition to any human residues. Human FR residues of immunoglobulin can be substituted with corresponding non-human residues. Accordingly, for example, in order to alter, generally to improve, antigen affinity or specificity, residues in the CDR or human framework region can be substituted with corresponding residues from the non-human CDR or framework region donor antibody. The humanized antibody can contain residues which cannot be found in the human antibody and donor CDR or framework sequence. For example, it can be predicted that FR substitution at a particular position which cannot be found in human antibody or donor non-human antibody can improve binding affinity or specific human antibody at this position. Antibody framework and CDR substitutions based on the molecular modeling are conventionally known in the technical field, for example by the modeling of interaction of CDR and framework residues to identify framework residues important for antigen binding and the sequence comparison for identifying unusual framework residues at the specific position (see e.g., U.S. Pat. No. 5,585,089; and Riechmann et al., Nature, 332:323 (1988)).

Chimeric antibodies are included in the TIM-3 antibody. According to this specification, the term "chimeric" and the grammatical variations thereof when it is used in relation to antibodies mean that amino acid sequence of the antibody contains one or more portion which is derived from two or more different species, is obtained or isolated from two or more different species or is based on two or more different species. For example, a portion of the antibody can be human (e.g., constant region) and other portion of the antibody can be non-human (e.g., a mouse heavy chain or a mouse light variable region). Accordingly, an example of the chimeric antibody includes an antibody in which the different portion of the antibody is derived from a different species. Different from the humanized or primatized antibody, the chimeric antibody can have a sequence of different species in an arbitrary region of the antibody.

The method for producing a chimeric antibody is known in the technical field (such as Morrison, *Science* 229: 1202 (1985); Oi et al., BioTechniques 4: 214 (1986); Gillies et al., *J. Immunol. Methods* 125: 191 (1989); U.S. Pat. Nos. 5,807,715; 4,816,567; and 4,816,397). For example, in Munro, *Nature* 312: 597 (1984); Neuberger et al., *Nature* 312: 604 (1984); Sharon et al., *Nature* 309: 364 (1984); Morrison et al., *Proc. Nat'l. Acad. Sci. USA* 81: 6851 (1984); Boulianne et al., *Nature* 312: 643 (1984); Capon et al, *Nature* 337: 525 (1989); and Traunecker et al., *Nature* 339: 68 (1989), a chimeric antibody in which a variable region of antibody derived from one species is replaced by a variable region of antibody derived from another species.

In addition, the anti-TIM-3 antibody can be prepared by hybridoma technique, recombinant technique, and phage display technique, and a combination thereof (see U.S. Pat. Nos. 4,902,614, 4,543,439, and 4,411,993; and also see *Monoclonal Antibodies*. Hybridomas: A New Dimensionin Biological Analyses, Plenum Press, Kennett, McKearn, and Bechtol et al, 1980, and Harlow et al., *Antibodies*: A Laboratory Manual, Cold Spring Harbor Laboratory Press, the second edition, 1988).

The human anti-human TIM-3 antibody of the invention was produced using chromosome-transferred mice (KM mice (trademark)) immunized with various forms of soluble form of recombinant human TIM-3 proteins or cell strains expressing TIM-3 (WO02/43478, WO02/092812, and Ishida et al., IBC's 11th Antibody Engineering Meeting, Abstract (2000)). The human anti-human antibody can not stain a non-transfected parent cell line but can stain detectably a human TIM-3 stable transfected cell line, such as Jurkat-TIM-3 cells and L929-TIM-3 cells.

The antibody of the invention can have κ light chain sequence or λ light chain sequence, full length of either one of them as present in naturally existing antibody, a mixture thereof (namely a fusion product of κ chain sequence and λ chain sequence) and subsequences/fragments thereof. The naturally presenting antibody molecules contain two κ light chains or two λ light chains.

In addition, the human TIM-3 antibody include an antibody which specifically binds to TIM-3 and does not inhibit or prevent the binding of rat anti-human TIM-3 antibody 344823 (manufactured by R&D Systems, catalogue No. MAB2365 or FAB2365P).

In addition, the anti-human TIM-3 antibody includes an antibody which specifically binds to TIM-3 and inhibits binding of the other anti-human TIM-3 antibody or does not inhibit binding of the other anti-human TIM-3 antibody.

The method for producing an antibody which specifically binds to TIM-3 can be provided as follows. In one embodiment, a method includes administering a human TIM-3, subsequence or fragment (such as extracellular region of TIM-3) conjugated with human Fc recombinant protein to an animal capable of expressing human immunoglobulin (e.g., a transgenic mice or transgenic cattle); screening the animal for expression of human TIM-3 antibody; selecting an animal that produces a human TIM-3 antibody; isolating an antibody from the selected animal. In one embodiment, using this method, one can determine whether the anti-human TIM-3 antibody has TIM-3 antagonist or agonist activity.

The invention further provides methods for producing human TIM-3 antibodies that inhibits or prevents TIM-3 binding to TIM-3 ligand (TIM-3L). In one embodiment, a method includes administering TIM-3, subsequence or fragment (such as extracellular region of TIM-3) conjugated with human Fc recombinant protein to an animal capable of expressing human immunoglobulin (e.g., a transgenic mice or transgenic cattle); screening the animal for expression of human TIM-3 antibody; selecting an animal that produces a human TIM-3 antibody; isolating an antibody from the selected animal. In one embodiment, using this method, one can determine whether the human TIM-3 antibody inhibits or prevents TIM-3 binding to TIM-3 ligand (TIM-3L).

As a method for controlling effector activity of the anti-TIM-3 monoclonal antibody of the invention, examples include a method which controls the amount of the fucose (also called core fucose) which is bound to N-acetylglucosamine (GlcNAc) through α-1,6 bond in a reducing end of a complex-type N-linked sugar chain which is bound to asparagine (Asn) at position 297 of an Fc region of an antibody (WO2005/035586, WO2002/31140, WO00/61739), a method in which is controlled by modifying amino acid residues of Fc region of the antibody, and the like. The effector activity can be controlled by applying any one of these methods to the anti-TIM-3 monoclonal antibody of the invention.

The effector activity means an antibody-dependent activity induced via Fc region of antibody, and such as antibody-dependent cellular cytotoxicity (ADCC activity), complement-dependent cytotoxicity (CDC activity), antibody-dependent phagocytosis (ADP activity) by phagocytes such as macrophage and dendritic cell, and the like, are known.

By controlling the content of the core fucose of complex-type N-linked sugar chain of Fc of the antibody, effector activity of the antibody can be increased or decreased. As a method for reducing the content of the fucose which binds to the complex-type N-linked sugar chain which is bound to Fc of the antibody, defucosylation can be mentioned. The defucosylation is to express an antibody using CHO cell from which α1,6-fucose transferase gene is deleted, and an antibody to which fucose is not bound can be obtained. The antibody to which fucose is not bound has high ADCC activity. On the other hand, as a method for increasing the content of the fucose which binds to the complex-type N-linked sugar chain to which Fc of the antibody is bound, the antibody to which fucose is bound can be obtained by expressing the antibody using a host cell in which α1,6-fucose transferase gene is introduced. The antibody to which fucose is bound has the ADCC activity lower than that of the antibody to which fucose is not bound.

In addition, ADCC activity and CDC activity can be increased or decreased by modifying amino acid residues of Fc of an antibody. For example, CDC activity of the antibody can be increased by using the amino acid sequence of the Fc region described in US 2007/0148165. Also, ADCC activity or CDC activity can be increased or decreased by carrying out the amino acid modification described in U.S. Pat. Nos. 6,737,056, 7,297,775 and 7,317,091.

Further, an antibody in which effector activity of the antibody is controlled can be obtained by using the above-mentioned methods in combination in one antibody.

The nucleic acid may have various lengths. The length of the nucleic acid encoding the TIM-3 antibody of the present invention or the subsequence thereof is generally about 100 to 600 nucleotides, or any numerical value or range within encompassing such lengths the above described range; 100 to 150, 150 to 200, 200 to 250, 250 to 300, 300 to 350, 350 to 400, 400 to 450, 450 to 500, 500 to 550 or 550 to 600 nucleotide length, or any numerical value or range or value within or encompassing such length the above described range. Examples of the length of nucleic acid which specifically hybridize with nucleic acid encoding the TIM-3 antibody of the present invention or the subsequence thereof include generally 10 to 20, 20 to 30, 30 to 50, 50 to 100, 100 to 150, 150 to 200, 200 to 250, 250 to 300, 300 to 400, 400 to 500, 500 to 600 nucleotides and any numerical value or range within or encompassing such length.

The terms "nucleic acid" and "polynucleotide" means at least two or more ribo- or deoxy-ribo nucleic acid base pairs (nucleotide) linked which are through a phosphoester bond or equivalent. The nucleic acid includes polynucleotide and polynucleoside. The nucleic acid includes a single molecule, a double molecule, a triple molecule, a circular molecule or a linear molecule. Examples of the nucleic acid include RNA, DNA, cDNA, a genomic nucleic acid, a naturally existing nucleic acid and a non-natural nucleic acid such as a synthetic nucleic acid, but are not limited. Short nucleic acids and polynucleotides (e.g., 10 to 20, 20 to 30, 30 to 50, 50 to 100 nucleotides) are commonly called "oligonucleotides" or "probes" of single-stranded or double-stranded DNA.

The nucleic acid can be prepared using various standard cloning techniques and chemical synthesis techniques. Examples of the techniques include, but are not limited to, nucleic acid amplification such as polymerase chain reaction (PCR), with genomic DNA or cDNA targets using primers (e.g., a degenerate primer mixture) which can be annealed with an antibody encoding sequence. In addition, nucleic acid can also be prepared by chemical synthesis (e.g., solid phase phosphoamidite synthesis) or transcription from a gene. The prepared sequence can be expressed by a cell (e.g., a host cell such as yeast, bacteria or eukaryote (an animal or mammal cell or a plant)) after it is translated in vitro or cloned into a plasmid and then amplified.

The vector is a vehicle which can be manipulated by insertion or incorporation of nucleic acid. Examples of the vector include a plasmid vector, a virus vector, a prokaryote (bacterium) vector and a eukaryote (plant, fungi, mammals) vector. The vector can be used for in vitro or in vivo expression of nucleic acid. Such a vector is called "expression vector" and is useful for the transfer of nucleic acid including a nucleic acid which encodes an TIM-3 antibody or its subsequence or fragment and the expression of an encoded protein by in vitro (e.g., in a solution or on solid phase), by a cell or by in vivo in a subject.

In addition, the vector can also be used for manipulation of nucleic acids. For genetic manipulation, an inserted nucleic acid can be transcribed or translated using a "cloning vector" in vitro (e.g., in a solution or on solid phase), in a cell or in vivo in a subject.

In general, the vector contains an origin of replication for amplification in a cell in vitro or in vivo. Control elements such as an expression control element present in the vector can be included in order to facilitate transcription and translation, if necessary.

A vector may include a selection marker. The "selection marker" is a gene which allows for the selection of a cell containing the gene. "Positive selection" means a process for selecting a cell containing the selection marker due to a positive selection. Drug resistance is an example of the positive selection marker, and a cell containing the marker will survive in culture medium containing the drug and a cell which does not contain the marker will die. Examples of the selection marker include drug resistance genes such as neo which provides resistance to G418; hygr which provides resistance to hygromycin; puro which provides resistance to puromycin, and the like. Other positive selection maker includes genes which enable identification or screening of a cell containing the marker. Examples of these genes include a fluorescent protein (GFP and GFP-like chromophore, luciferase) gene, lacZ gene, alkaline phosphatase gene, and a surface marker such as CD8. "Negative selection" means a process for killing cells which contain negative selection markers by exposing to an appropriate negative selection agent. For example, a cell containing a herpes simplex virus thymidine kinase (HSV-tk) gene (Wigler et al., Cell, 11: 223 (1977)) is sensitive to a drug ganciclovir (GANC). Similarly, gpt gene makes a cell sensitive to 6-thioxantine.

The virus vector includes those which are based on retroviral (a lentivirus for infecting not only dividing cells but also non-dividing cells), foamy virus (U.S. Pat. Nos. 5,624,820, 5,693,508, 5,665,577, 6,013,516 and 5,674,703; WO 92/05266 and WO 92/14829), adenovirus (U.S. Pat. Nos. 5,700,470, 5,731,172 and 5,928,944), adeno-associated virus (AAV) (U.S. Pat. No. 5,604,090), a herpes simplex virus vector (U.S. Pat. No. 5,501,979), a cytomegalovirus (CMV) system vector (U.S. Pat. No. 5,561,063), reovirus, rotavirus genome, simian virus 40 (SV40) or papilloma virus (Cone et al., Proc. Natl. Acad. Sci. USA, 81:6349 (1984); Eukaryotic Viral Vectors, Cold Spring Harbor Laboratory, edited by Gluzman, 1982; Sarver et al., Mol. Cell. Biol., 1: 486 (1981); U.S. Pat. No. 5,719,054). Adenovirus efficiently infects a slowly replicating and/or terminally differentiated cell, and can be used to target the slowly replicating cell and/or terminally differentiated cell. Additional examples of virus vectors useful for expression include parbovirus, Norwalk virus, corona virus, paramyxo virus and rhabdo virus, toga virus (e.g., Sindobis virus and Semliki forest virus) and vesicular stomatitis virus (VSV).

A vector comprising a nucleotide acid can be expressed when the nucleic acid is connected to expression elements so as to function. The term "connected so as to function" (operably linked) means that a physical or functional relation between the elements referred to that permit them to operate in their intended fashion. Accordingly, the nucleic acid "operably linked" to an expression control element means that the control element modulates nucleic acid transcription and, as appropriate, translation of the transcription product.

The "expression control element" or "expression control sequence" is a polynucleotide which influences upon expression of an operably linked nucleic acid. Promoters and enhancers are non-limiting specific examples of expression controlling elements and sequences. The "promoter" is a cis-acting DNA regulatory region which can initiate transcription of downstream (3' direction) nucleic acid sequence. A nucleotide which accelerates transcription initiation is included in the promoter sequence. The enhancer also regulates nucleic acid expression but acts at a distance from the transcription initiation site of the nucleic acid to which it is operably linked. When the enhancer is present in either 5' or 3' end of the nucleic acid as well as within the nucleic acid (e.g., intron or coding sequence), the enhancer further functions. Additional examples of the expression control element include a leader sequence and a fusion partner sequence, an internal ribosome entry site (IRES) element for preparing multigene, or polycistronic message, splicing signal of intron, maintenance of correct reading frame of gene to enable inframe translation of mRNA, polyadenylation signal which produces proper polyadenylation of the transcription product of interest, and stop codons.

Examples the expression control element include a "constitutional" element in which transcription of an operably linked nucleic acid occurs without the presence of signals or stimulus. The expression control element which confers expression in response to the signal or stimulus and increase or decrease expression of the operably linked nucleic acid is "adjustable". The adjustable element which increases expression of the operably linked nucleic acid in response to a signal or stimulus is called an "inducible element". The adjustable element which decreases expression of the operably linked nucleic acid in response to a signal or stimulus is called "repressor element" (namely, the signal decreases the expression; and the expression increases when the signal is removed or not present).

Examples of the constitutional promoter for bacterial expression include an inducing promoter, such as T7 and pL, plac, ptrp and ptac (ptrp-lac hybrid promoter) of bacteriophage λ and the like. For insect cell system, a constitutional or inducible promoter (e.g., ecdysone) can be used. The constitutional promoter for yeast, include an inducing promoter such as ADH, LEU2, GAL and the like (e.g., see Ausubel et al., In: *Current Protocols in Molecular Biology*, Vol. 2, Chapter 13, Greene Publish. Assoc. & Wiley Interscience edition, 1988; Grant et al., In: *Methods in Enzymology*, 153: 516-544 (1987) Wu & Grossman, 1987, Acad. Press, N.Y.; Glover, *DNA Cloning*, Vol. 11, Chapter 3, IRL Press, Wash., D.C., 1986; Bitter, In: *Methods in Enzymology*, 152: 673-684 (1987), edited by Berger & Kimmel, Acad. Press, N.Y.; and Strathern et al., The *Molecular Biology of the Yeast Saccharomyces*, edited by Cold Spring Harbor Press, Vol. 1 and Vol. 11 (1982)).

For the expression in mammals, a constitutional promoter derived from a virus or other origin can be used. For example, inducible promoters derived from CMV, SV40, or a viral long terminal repeated sequence (LTR), or mammal cell genome (e.g., metallothionein IIA promoter; heat shock promoter, steroid/thyroid hormone/retinoic acid responding element) or mammal virus (e.g., adenovirus late promoter; mouse breast cancer virus LTR) can be used.

Examples of the expression control element include an element which is active in a specific tissue or cell types, and such an element is called "tissue specific expression control element". In general, the tissue specific expression control element is more active in specific cells or tissue types, and this is because this tissue specific expression control element is recognized by a transcription activating protein which is active in the specific cell or tissue types or by other transcription factor, as compared to other cells or tissue types. Non-limiting specific examples of such an expression control element are hexokinase II, COX-2, α-fetoprotein, carcinoembryonic antigen, DE3/MUC1, prostate specific antigen, C-erB2/neu, glucose-dependent insulin secretion stimulatory polypeptide (GIP), telomerase reverse transcriptase and a promoter such as hypoxia-responsive promoter.

According to the invention, a host cell transformed or transfected with TIM-3 nucleic acid or vector is provided. Examples of the host cells, but are not limited to, include prokaryotic cell and eukaryotic cell, such as, bacteria, fungi (yeast), and cells of plants, insects and animals (e.g., mammals such as primates, human and the like). Non-limiting examples of transformed cell include a bacteria transformed with a recombinant bacteriophage nucleic acid, a plasmid nucleic acid or cosmid nucleic acid expression vector; a yeast transformed with a recombinant yeast expression vector; a plant cell infected with a recombinant virus expression vector (e.g., cauliflower mosaic virus, CaMV; tobacco mosaic virus, TMV) or transformed with a recombinant plasmid expression vector (e.g., Ti plasmid); an incest cell infected with a recombinant virus expression vector (e.g., baculovirus); and an animal cell infected with a recombinant virus expression vector (e.g., retrovirus, adenovirus, vaccinia virus) or a transformed animal cell manipulated for stable expression. A CHO cell is a non-limiting example of a mammal host cell which expresses a TIM-3 antibody and its subsequence thereof and fragment. The host cell may be a plurality or population of cells from a primary cell isolated strain, an isolated secondary cell or subcultured cell, or an established cell line or immortalized cell culture.

The term "be transformed" or be transfected" when it is used in reference to a cell (e.g., host cell) or an organism means a change of gene in a cell after incorporation of an exogenous molecule, such as a protein or a nucleic acid (e.g., transgene), into the cell. Accordingly, the "transfected" or "transformed" cell is a cell into which the exogenous molecule is introduced by the hand of man, for example, recombinant DNA techniques or a progeny thereof.

The nucleic acid or protein can be transfected or transformed (expressed) in the cell or a progeny thereof stably or temporarily. The introduced protein can be expressed by growing the cell, or transcribing the nucleic acid. Since there is a possibility that a mutation occurs during replication, there is a case that a progeny of the transfected or transformed cell is not identical to the parent cell.

In general, a vector is used in the cell transfection or transformation. The vector can be included in a viral particle or vesicle and can be optionally directed demands to a specific cell types by including a protein on the particle or vesicle surface which binds to a target cell ligand or receptor. Accordingly, a cell can be used as a target by preparing the viral particle or vesicle itself or the viral surface protein, for the purpose of an in vitro, ex vivo or in vivo transfection or transformation. Therefore, the vector includes in vitro, in vivo and ex vivo delivering techniques of viral and non-viral vectors into a cell, tissue or organ.

In addition, introduction of a nucleic acid into a target cell (e.g., a host cell) can also be carried out by a method conventionally known in the technical field, such as osmotic shock (e.g., calcium phosphate), electroporation, microinjection, cell fusion and the like. The introduction of nucleic acid and polypeptide in vitro, ex vivo and in vivo can also be carried out using other techniques. For example, a polymer substance such as polyester, poyamic acid, hydrogel, polyvinyl pyrrolidone, ethylene-vinyl acetate, methyl cellulose, carboxymethylcellulose, protamine sulfate, or lactide/glycolide copolymer, polylactide/glycolide copolymer, or ethylene vinyl acetate copolymer and the like can be used. The nucleic acid can be enclosed in a microcapsule using a hydroxymethyl cellulose or gelatin-microcapsule or poly (methyl methacrylate)-microcapsule, or a colloid system, respectively, by a coacervation technique or by interfacial polymerization. The colloid dispersion system includes a system based on a polymer complex, nanocapsule, microsphere, beads and lipid (oil-in-water type emulsion, micelle, mixed micelle, liposome and the like).

The liposome for introducing various compositions into cells is conventionally known in the technical field, and for example, phosphatidylcholine, phosphatidylserine, lipofectin and DOTAP are included therein (e.g., U.S. Pat. Nos. 4,844,904, 5,000,959, 4,863,740 and 4,975,282; and GIBCO-BRL, Gaithersburg, Md.). Piperazine based amphilic cationic lipids which is useful in gene therapy (see e.g., U.S. Pat. No. 5,861,397) are also known. A cationic lipid system is also known (see e.g., U.S. Pat. No. 5,459, 127). In this specification, the polymer substance, microcapsule and colloid dispersion system (liposome and the like) are collectively called as "vesicle".

In addition, examples of the suitable techniques which can be used in the method for an antibody are affinity purification, non-modified gel purification, HPLC or RP-HPLC, size exclusion, purification by protein A column and an optional combination of these techniques. An anti-TIM-3 antibody isotype can be determined using ELISA assay, and for example, human Ig can be identified using mouse Ig absorbed anti-human Ig.

The binding affinity can be determined by association (Ka) and dissociation (Kd) rates. The equilibrium affinity constant KD is the ratio of Ka/Kd. The association (Ka) and dissociation (Kd) rates can be measured using surface plasmon resonance (SPR) (Rich and Myszka, *Curr. Opin. Biotechnol.*, 11: 54 (2000): Englebienne, Analyst., 123: 1599 (1998)). Instrumentation and methods for real time detection and monitoring of association rate are conventionally known and commercially available (BiaCore 2000, Biacore AB, Upsala, Sweden; and *Malmqvist, Biochem. Soc. Trans.*, 27:335 (1999)). The KD value can be defined as the TIM-3 antibody concentration required to saturate one half of the binding site (50%) on TIM-3.

(Pharmaceutical Composition)

Antibodies can be included in a pharmaceutical composition. In an embodiment, an antibody comprises a pharmaceutically acceptable carrier, a stabilizer or a filler and is prepared in the form of aqueous solution or as a freeze-dried preparation. Typically, an appropriate amount of a pharmaceutically acceptable salt is used for isotonicity of the pharmaceutical preparation. Examples of the acceptable carrier, stabilizer or filler include a buffer solution such as phosphate, citrate and other organic acid and the like; a low molecular weight (less than 10 in the number of residues) polypeptide; a protein such as serum albumin, gelatin, immunoglobulin and the like; a hydrophilic polymer such as polyvinyl pyrrolidone; an amino acid such as glycine, glutamine, asparagine, histidine, arginine, lysine and the like; a monosaccharide such as glucose, mannose, dextrin and the like, disaccharides and other carbohydrates; a chelating agent such as EDTA and the like; saccharides such as sucrose, mannitol, trehalose, sorbitol and the like; a salt forming counter ion such as sodium and the like; an antioxidant including methionine and ascorbic acid; a metal complex (e.g., Zn-protein complex); an antiseptic (octadecyl dimethylbenzylammonium chloride; hexamethonium chloride; banzalconium chloride; benzethonium chloride; phenol, butyl or benzyl alcohol; alkyl parabens such as methyl or propyl paraben; catechol; resorcinol; cyclohexanol; 3-pentanol; and m-cresol); and/or a nonionic surfactant such as TWEEN™, PLURONICS™, polyethylene glycol (PEG) and the like.

(Therapeutic Use of Antitumor Substance which Target TIM-3 Expression Cells)

Examples of the antitumor substances targeting TIM-3 expressing cells are anti-TIM-3 antibodies, but are not limited to.

Examples of the diseases for which the therapeutic use is examined, but are not limited thereto, include the diseases which can be considered to treat by binding or targeting TIM-3-expressing blood tumor cells (AML cell, CML cell, MDS cell, ALL cell, CLL cell, Multiple Myeloma cell and the like), helper T cell (e.g., Th1 cell, Th17 cell) antigen presenting cell (e.g., dendritic cell, monocyte macrophage and related cells (hepatic stellate cell, osteoclast, microglia, intraepidermal macrophage, dust cell (alveolar phagocyte) and the like)). Examples of the disease for which therapeutic use is examined include a blood disease, especially hematologic tumor, in which expression of TIM-3 is found in bone marrow or peripheral blood. Specific example may include acute myelocytic leukemia AML). Based on the FAB classification (French-American-British criteria) which can determine which stage of the cell among the cells in the course of differentiating into various blood cells from the hematopoietic stem cell caused tumorigenic transformation, the acute myelocytic leukemia is classified into disease types of M0 (micro-differentiation type myeloblastic leukemia), M1 (undifferentiated myeloblastic leukemia), M2 (differentiated myeloblastic leukemia), M3 (acute promyelocytic leukemia), M4 (myelomonocytic leukemia), M5 (monocytic leukemia), M6 (erythroleukemia), M7 (megakaryocytic leukemia) and subtypes thereof. In addition, further examples of diseases include acute lymphocytic leukemia, atypical leukemia, chronic myelocytic leukemia, chronic lymphocytic leukemia, adult T cell leukemia, NK/T cell lymphoma, granular lymphocytosis (LGL leukemia), polycythemia vera, essential thrombocythemia, hypereosinophilic syndrome, myelodysplastic syndrome, lymphoma (such as Hodgkin lymphoma, non-Hodgkin lymphoma, B-cell lymphoma (such as follicular lymphoma, MALT lymphoma, mantle cell lymphoma, diffuse large B-cell lymphoma, Burkitt lymphoma, lymphoblastic lymphoma and Catsleman disease), T cell lymphoma (T/NK cell lymphoma, adult T cell leukemia and NK/T cell lymphoma).

The method of the invention which comprises administration or delivery of an anti-TIM-3 antibody and an antitumor substance which targets a TIM-3 expression cell can be carried out by any acceptable method. In a specified embodiment, these are administered to a subject, locally, regionally or systemically.

In addition, regarding the TIM-3 antibody or the antitumor substance which targets TIM-3 expression cell for treating the above-mentioned diseases can also be considered to combine with other therapeutic agent suitable for the same disease (typically a chemotherapeutic agent) or be administered in combination with radiotherapy.

Examples of the suitable other therapeutic agent include a chemotherapeutic agent such as cytarabine (Ara-C), an anthracycline system antitumor agent (typically, daunorubicin (DNR), idarubicin (IDA)) and the like, a differentiation inducing therapeutic agent such as all-trans retinoic acid (ATRA), arsenious acid, and Am80 (tamibarotene), gemtuzumab-ozogamicin (ozogamicin conjugate anti-CD33 antibody), topotecan, fludarabine, cyclosporine, mitoxantrone (MIT), interferon and imatinib, but are not limited thereto, and also include a combination with a therapeutic method considered to be clinically effective.

Mammals (e.g., human) are included in the subject which can be treated by the invention. In a specified embodiment, it is a subject who is a candidate of blood tumor or who received treatment of the blood tumor, a subject who is a candidate of a blood tumor and in whom TIM-3 expressing cells are detected, a subject having a possibility causing TIM-3-mediated cellular response or who received treatment of the TIM-3-mediated cellular response, a subject who is a candidate of a myelocytic malignant tumor or who received treatment of the myelocytic malignant tumor or a subject who is a candidate of acute myelocytic leukemia or who received treatment of the acute myelocytic leukemia.

According to this specification, the terms "treat", "treating", "treatment" and the grammatical variations thereof mean a protocol, a planning, a process or an improving method which is carried out on each subject who is desirable to obtain physiological effect or good outcome on the patient. Accordingly, the method of the invention includes a treatment and a treating method which produce measurable improvement or beneficial effect, particularly on a disorder, a disease, pathology, a condition of a disease or a symptom of a given subject. The measurable improvement or profitable effect is objective or subjective, transient or long-term improvement of any one of disorders, diseases, phisiological conditions, conditions of a disease or symptoms, or a reduction in onset, severity, duration or frequency of adverse symptom related to or caused by disorders, diseases, physiological conditions, conditions of a disease or state. According to the method of the invention, there is a possibility that its effect is not always exhibited immediately, but eventual improvement or beneficial effect is found a little later with the lapse of time, so that stabilization or amelioration in a give subject will occur.

In the specification, the term "recurrence" refers to the condition in which symptoms worsen or a subject gets into non-remission state after the therapy is once successful or induces remission in terms of hematology. The "remission" in leukemia refers to the conditions in which any blast of leukemia cells are not found in peripheral blood. The proposed remission state in acute myeloid leukemia is defined by NIH (see Cheson B D, et al., Journal of Clinical Oncology, Vol. 8, 813-819). In addition, the term "refractory" refers to the condition in which effects due to treatment are not found in a subject.

(Antagonist)

Antibodies further include those that affect a function or activity of TIM-3. In particular embodiments, an antibody inhibits or prevents the binding of TIM-3 ligand to TIM-3; inhibits or prevents the binding of TIM-3 ligand to cell; modulate TIM-3-mediated cell signaling (e.g., inhibits or prevents); modulate TIM-3-mediated cell response. In particular aspects, a TIM-3-mediated cell response comprises proliferation of TIM-3 expressing cell, promotion of production of cytokine such as IFNγ and enhancement of tumor immunity.

(Use of Agonist Antibody)

Antibodies further include those that affect a function or activity of TIM-3. In particular embodiments, an antibody mimic the binding of TIM-3 ligand to TIM-3; modulate (e.g., promote or enhance) TIM-3-mediated signal transduction; modulate TIM-3-mediated cell response. The TIM-3 expressing cell response induces growth arrest of TIM-3 expressing cell, controlling of production of cytokines and the like.

Unless otherwise noted, all of the technical terms and scientific terms used in this specification have the same meanings of those which are generally evident for persons in the technical field to which the invention is related. Methods and materials similar or equivalent to those described in this specification can be used in the operations or examinations of the invention, but those which are described in this specification are suitable methods and materials.

EXAMPLES

Example 1

Preparation of Bone Marrow and Peripheral Blood Cells

Provision of the analytes from patients and healthy volunteers was carried out under the recognition by an ethical committee at the Kyushu University Hospital. The bone marrow cell was collected by a bone-marrow aspiration from a patient of leukemia or myelodysplastic syndrome and a healthy volunteer. The peripheral blood was collected by an intravenous blood collection from a healthy volunteer. The stem cell-mobilized peripheral blood was collected from a patient indicated for autologous peripheral blood stem cell transplantation (a case in which a patient has a relapse of a diffuse large cell type B cell lymphoma after entering into complete remission with chemotherapy and has sensitivity for the chemotherapy). Specifically, after completion of chemotherapy (Cyclophosphamide (CY) massive dose therapy or VP-16 (etoposide) massive dose therapy), peripheral blood stem cells were mobilized by the administration of a G-CSF preparation (Filgrastim), GRAN® (Kyowa Hakko Kirin Co., Ltd.) and collected using a standard apheresis. A portion of mononuclear cells collected to confirm the existance of CD34 positive cells was used for experiment. In this connection, the dose and schedule of drugs were standard protocol covered by insurance.

Heparin was added to the collected cells to prevent coagulation. After dilution of each analyte with PBS, Ficoll-Plaque Plus (GE Healthcare) was spread under it. The mononuclear cells were separated from serum and platelets by carrying out centrifugation at 1700 rpm for 30 minutes (a brake was not applied). The boundary containing PBMC was collected and washed using a staining medium. After suspension with the staining medium again, the cells were mixed with Türk solution and then counted. The cells were re-suspended using 100 μl of the staining medium per $1 \times 10^6$ cells. To stain normal hematopoietic stem cells and precursor cells, positive selection of CD34 positive cells was carried out using Indirect CD34 MicroBead Kit (Miltenyi Biotec) after the above-mentioned mononuclear cell separation and then the staining medium was added to give a final volume of 100 μl.

Example 2

Staining and Analyzing Methods of Bone Marrow Normal Hematopoietic and Tumor Stem Cells The cells were stained using 2 μl of an anti-human CD34 antibody (manufactured by Becton Dickinson & Co., (hereinafter referred to as BD), Cat No. 340441), 20 μl of anti-human CD38 antibody (manufactured by CALTAG, Cat No. MHCD3815), 2 μl of anti-human CD90 antibody (manufactured by BD, Cat No. 555595) or 20 μl of anti-TIM-3 antibody (manufactured by R & D Systems, 344823) as the primary antibodies at 4° C. for 40 minutes. Then, PBS was added for wash, and the obtained suspension was centrifuged at 1500 rpm for 5 minutes. After the supernatant was discarded, 100 μl of the staining medium was added thereto. The obtained cells were stained by adding 5 μl of each of anti-human Lineage antibodies (anti-human CD3 (manufactured by BD, Cat No. 555341), CD4 (manufactured by BD, Cat No. 555348), CD8 (manufactured by BD, Cat No. 555636), CD10 (manufactured by BD, Cat No. 555376), CD19 (manufactured by BD, Cat No. 555414), CD20 (manufactured by BD, Cat No. 555624), CD11b (manufactured by BD, Cat No. 555389), CD14 (manufactured by Beckman Coulter, Cat No. A07765), CD56 (manufactured by BD, Cat No. 555517) and GPA (manufactured by BD, Cat No. 559944) antibodies as the secondary antibody, and 5 μl of streptoavidin APC-Cy7 (manufactured by BD, Cat No. 554063) at 4° C. for 40 minutes. After washing with PBS, the obtained cells were re-suspended with PI-containing staining medium. Analysis and sorting of the analytes were carried out by FACSAria (BD).

Example 3

Expression of Human TIM-3 Molecule in Human Blood Tumor

Expression of human TIM-3 molecule in human blood tumor was examined using the methods of Example 1 and Example 2.

Expression of human TIM-3 molecule in AML (M0) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 1 and Table 1. In the patients with AML (M0), expression of TIM-3 was observed in one of the two cases. Accordingly, this example showed usefulness of TIM-3 as a therapeutic target for AML (M0) cells.

Figure 2:
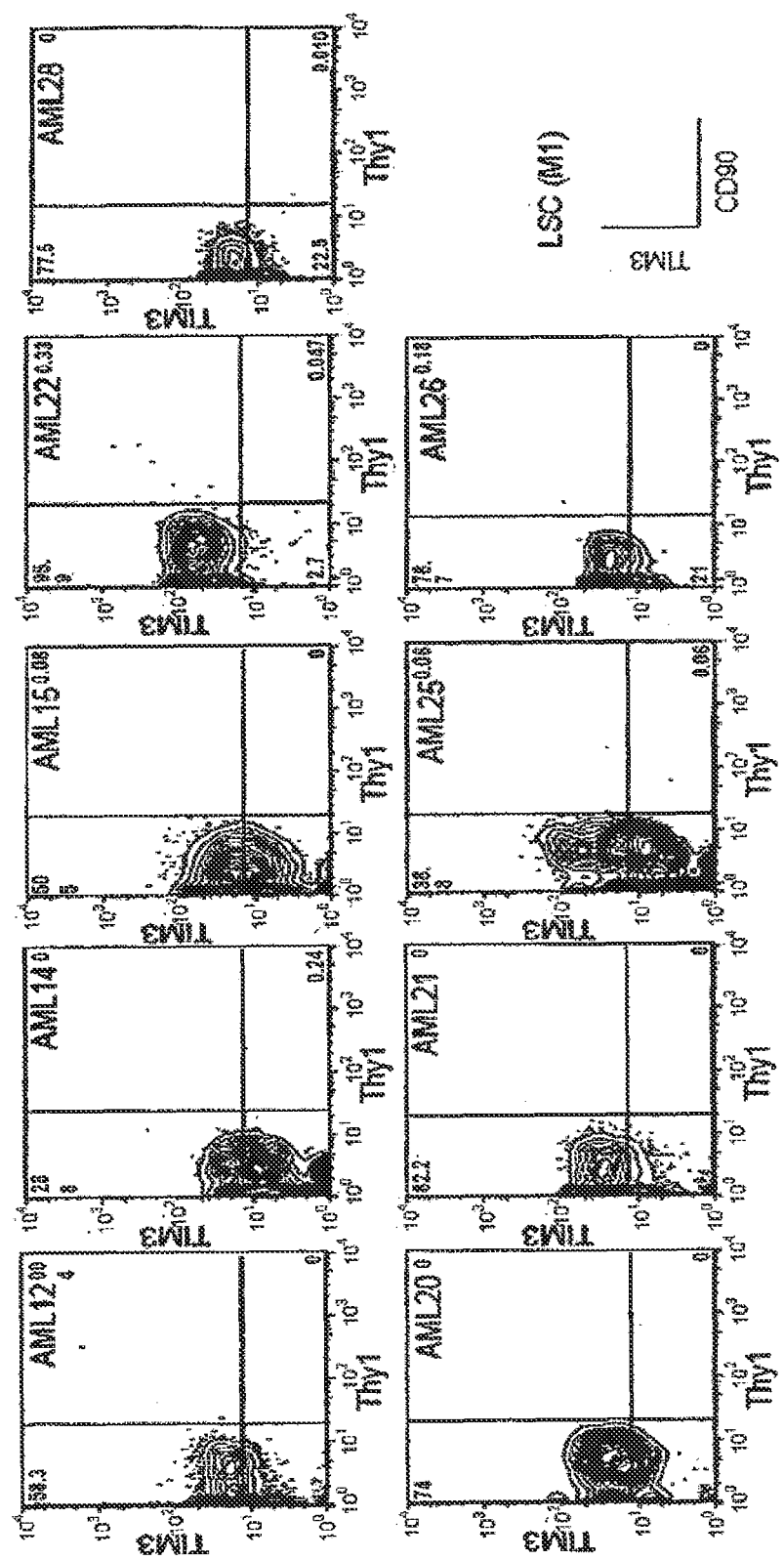
FIG. 2 shows a result of multicolor flow cytometric analysis of expression of human TIM-3 molecule on bone marrow Lin(−)CD34(+)CD38(−) cells derived from an AML (M1) patient.

Expression of human TIM-3 molecule in AML (M1) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 2 and Table 1. In the patients with AML (M1), expression of TIM-3 was observed in all nine cases. Accordingly, this example showed usefulness of TIM-3 as a therapeutic target for AML (M1) cells.

TABLE 1

| | | | % of TIM-3(+) cells | | |
| Pt | FAB | Cytogenetic Abnomality | Lin(−)CD34(+) CD38(−) | Lin(−)CD34(+) CD38(+) | Lin(−) CD34(−) |
| --- | --- | --- | --- | --- | --- |
| AML1 | M2 | t(8;21) | 89.4 | 85.7 | 45 |
| AML2 | M2 | 46XY | 49.7 | 94.7 | 44.6 |
| AML3 | M4 | 46XY | 86 | 84.4 | 82.4 |
| AML4 | M2 | 46XX | 83.3 | 90.6 | 81.8 |
| AML5 | M0 | | 4.2 | 1.1 | 4.4 |
| AML6 | M2 | | 77.5 | 82.9 | 30 |
| AML7 | M5 | | 66.7 | 58.4 | 82.2 |
| AML8 | M2 | | 60.6 | 89 | 62.1 |
| AML9 | M2 | | 96.5 | 91 | 64 |
| AML10 | M4 | | 99.9 | 98.5 | 71.2 |
| AML11 | M3 | PML/RARa | 1.6 | 22.7 | 52.2 |

TABLE 1-continued

| | | | % of TIM-3(+) cells | | |
| Pt | FAB | Cytogenetic Abnomality | Lin(−)CD34(+) CD38(−) | Lin(−)CD34(+) CD38(+) | Lin(−) CD34(−) |
| --- | --- | --- | --- | --- | --- |
| AML12 | M1 | 46XY | 64.4 | 73.5 | 36.7 |
| AML13 | M2 | t(8;21) | 65.7 | 69 | 43.9 |
| AML14 | M1 | | 26.6 | 23.3 | 19 |
| AML15 | M1 | | 50.3 | 69.1 | 50.8 |
| AML16 | M4 | inv 16 | 93.7 | 94.2 | 30.1 |
| AML17 | M2 | | 91.2 | 93.5 | 36.1 |
| AML18 | M5 | | 2.3 | 37.7 | 80.3 |
| AML19 | M6 | | 18 | 34.6 | 37.6 |
| AML20 | M1 | Flt3-ITD+ | 74 | 76.3 | 32 |
| AML21 | M1 | Flt3-ITD+ | 82.2 | 90.5 | 85 |
| AML22 | M1 | | 97.2 | 98 | 93.1 |
| AML23 | M2 | | 94.2 | 94.7 | 40 |
| AML24 | M0 | | 97.8 | 99.4 | 69.6 |
| AML25 | M1 | | 38.8 | 65.8 | 33 |
| AML26 | M1 | | 72.5 | 83.1 | 34.9 |
| AML27 | M4 | Flt3-ITD+ | 84.9 | 90.1 | 78 |
| AML28 | M1 | | 74.6 | 77.7 | 33.4 |
| AML29 | M2 | | 98.3 | 99.1 | 79.2 |
| AML30 | M6 | | 35.5 | 53.6 | 24.5 |
| AML31 | M4 | | 56.1 | 68.5 | 77.7 |

Figure 3:
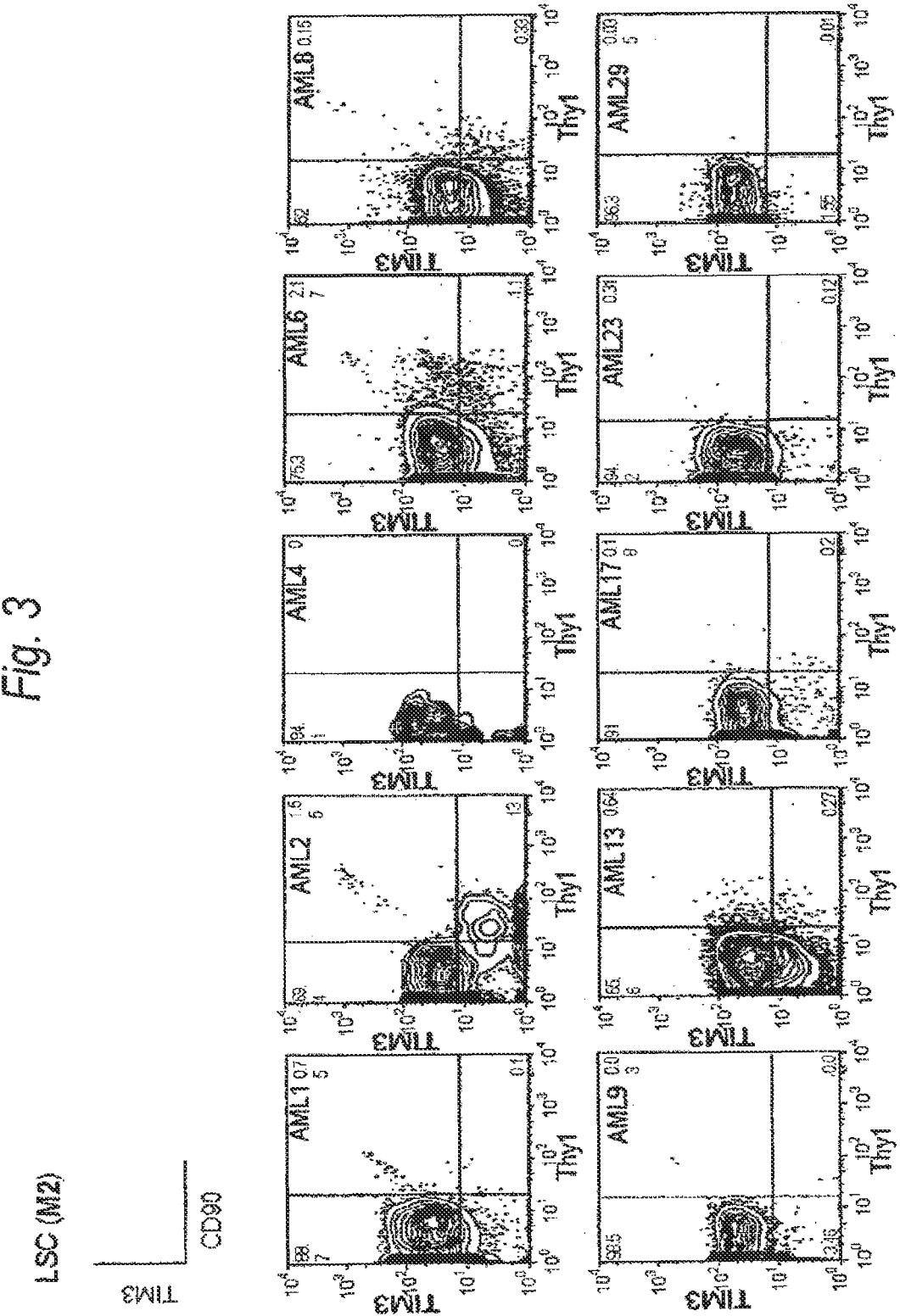
FIG. 3 shows a result of multicolor flow cytometric analysis of expression of human TIM-3 molecule on bone marrow Lin(−)CD34(+)CD38(−) cells derived from an AML (M2) patient.

Expression of human TIM-3 molecule in AML (M2) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 3 and Table 1. In the patients with AML (M2), expression of TIM-3 was observed in all ten cases. Accordingly, this example showed usefulness of TIM-3 as a therapeutic target for AML (M2) cells.

Figure 4:
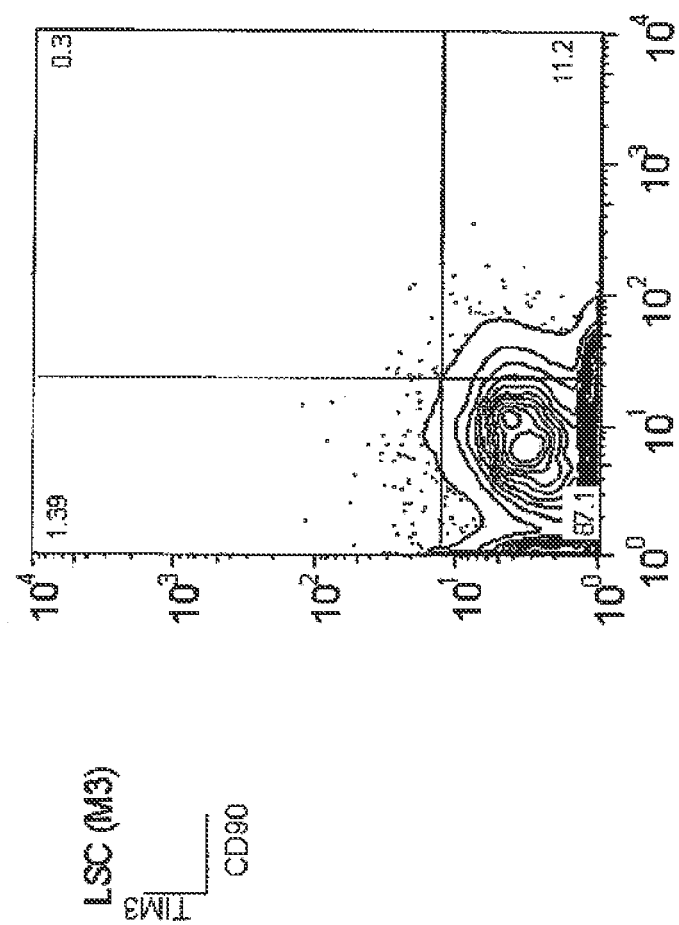
FIG. 4 shows a result of multicolor flow cytometric analysis of expression of human TIM-3 molecule on bone marrow Lin(−)CD34(+)CD38(−) cells derived from an AML (M3) patient.

Expression of human TIM-3 molecule in AML (M3) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 4 and Table 1. In the patient with AML (M3), expression of TIM-3 was observed in one case. Accordingly, this example showed usefulness of TIM-3 as a therapeutic target for AML (M3) cells.

Figure 5:
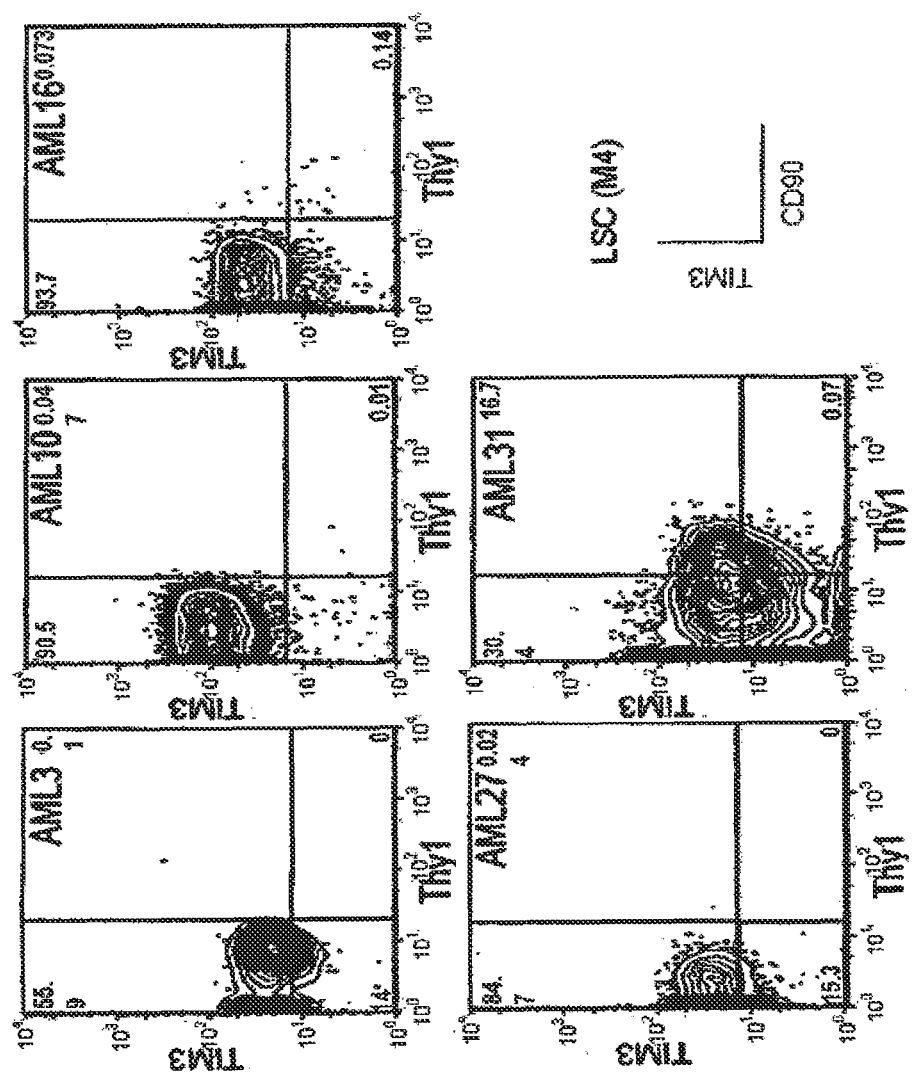
FIG. 5 shows a result of multicolor flow cytometric analysis of expression of human TIM-3 molecule on bone marrow Lin(−)CD34(+)CD38(−) cells derived from an AML (M4) patient.

Expression of human TIM-3 molecule in AML (M4) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 5 and Table 1. In the patients with AML (M4), expression of TIM-3 was observed in all five cases. Accordingly, this example showed usefulness of TIM-3 as a therapeutic target for AML (M4) cells.

Figure 6:
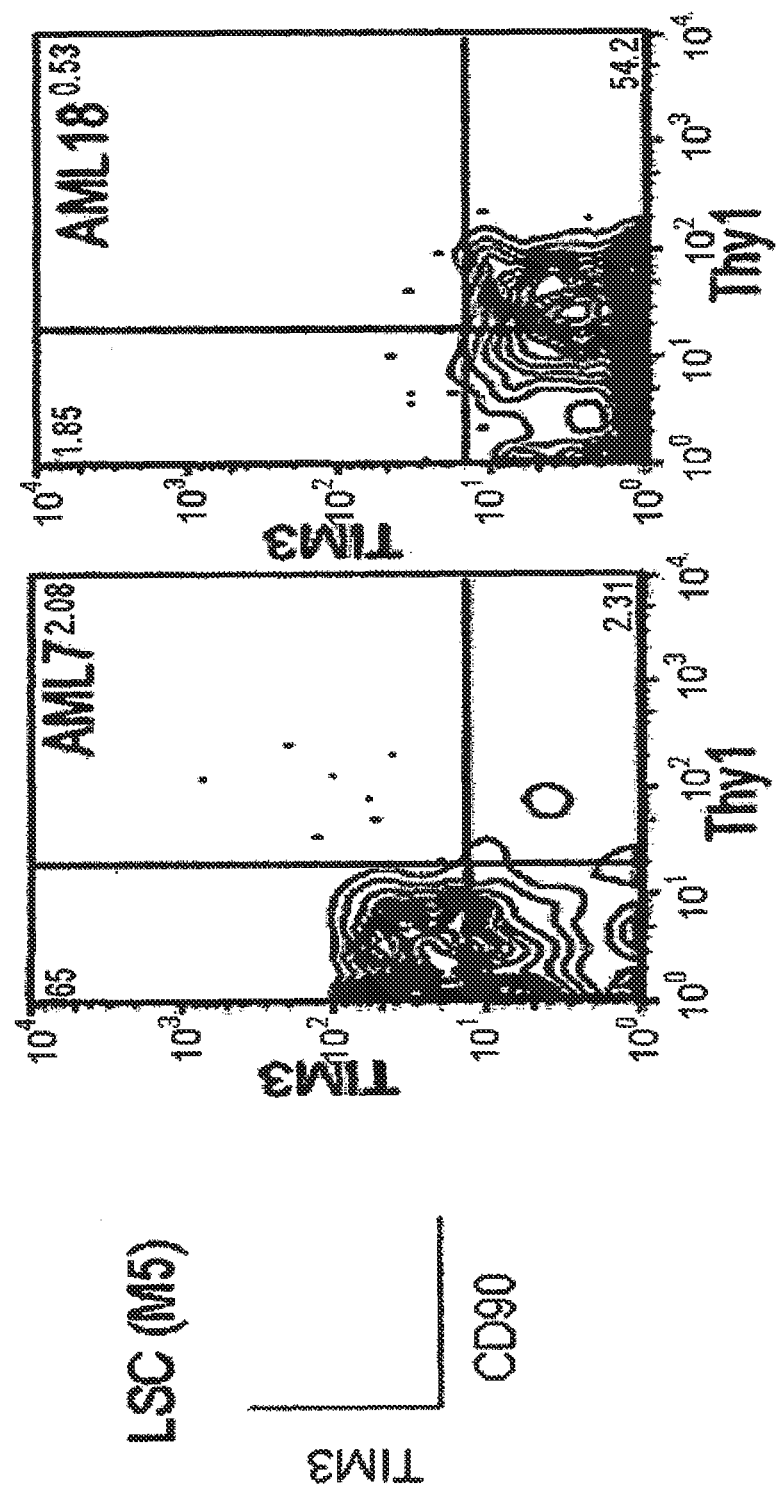
FIG. 6 shows a result of multicolor flow cytometric analysis of expression of human TIM-3 molecule on bone marrow Lin(−)CD34(+)CD38(−) cells derived from an AML (M5) patient.

Expression of human TIM-3 molecule in AML (M5) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 6 and Table 1. In the patients with AML (M5), expression of TIM-3 was observed in all two cases. Accordingly, this example showed usefulness of TIM-3 as a therapeutic target for AML (M5) cells.

Figure 7:
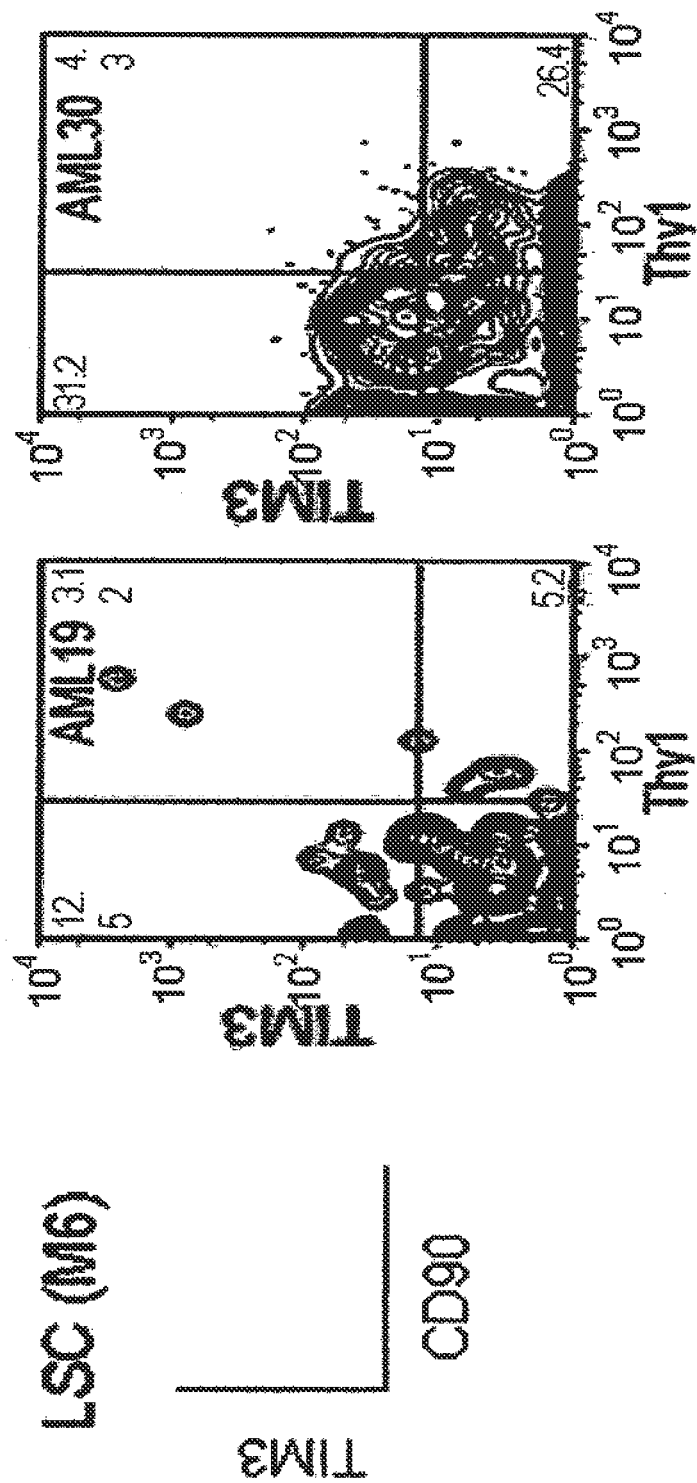
FIG. 7 shows a result of multicolor flow cytometric analysis of expression of human TIM-3 molecule on bone marrow Lin(−)CD34(+)CD38(−) cells derived from an AML (M6) patient.

Expression of human TIM-3 molecule in AML (M6) patient-derived bone marrow Lin(−)CD34(+)CD38(−) cell, Lin(−)CD34(+)CD38(+) cell and Lin(−)CD34(−) cell was examined by analysis using multicolor flow cytometry. The results are shown in FIG. 7 and Table 1. In the patients with AML (M6), expression of TIM-3 was observed in all two cases. Accordingly, this example showed usefulness of TIM-3 as a therapeutic target for AML (M6) cells.

Figure 9:
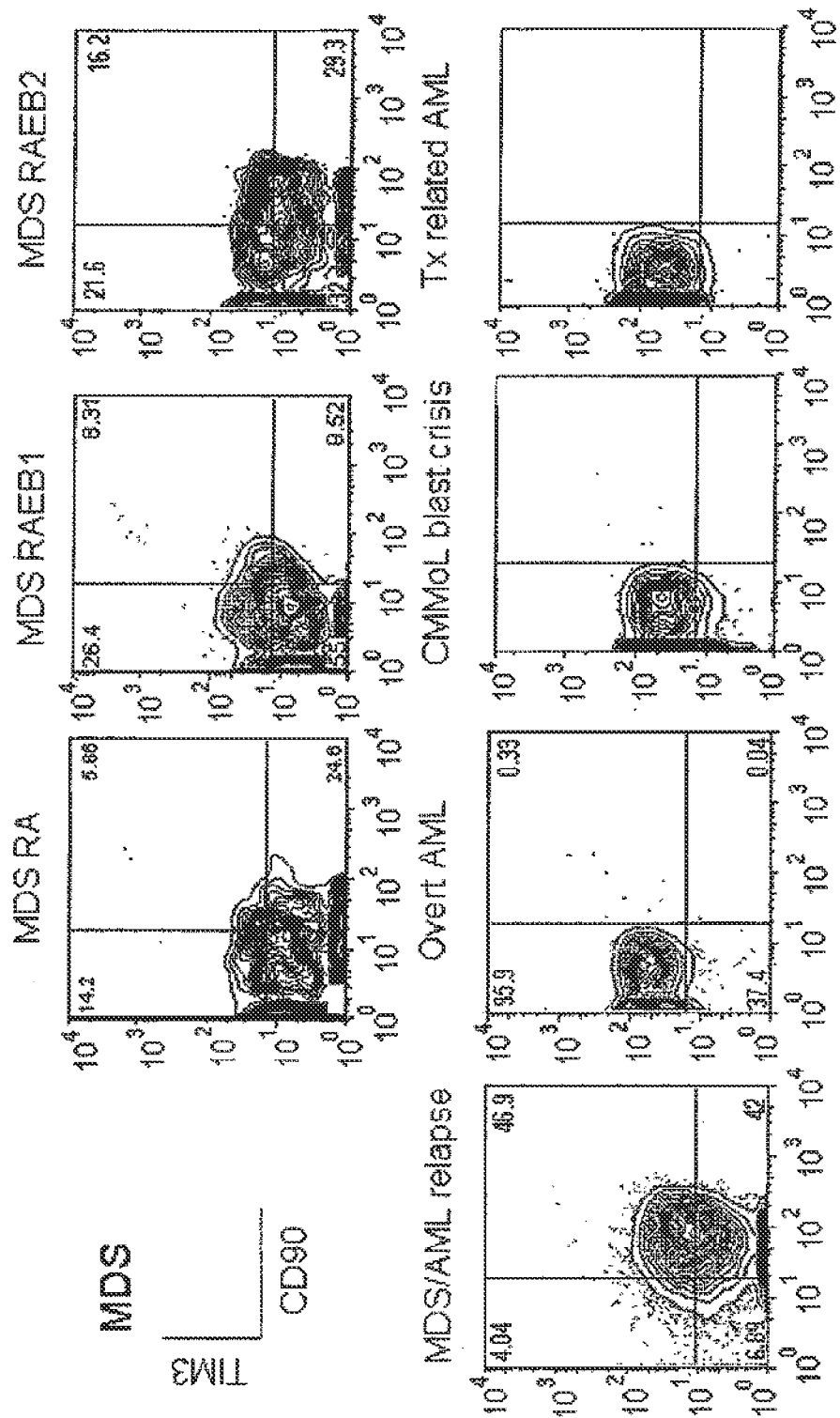
FIG. 9 shows a result of multicolor flow cytometric analysis of expression of human TIM-3 molecule on bone marrow Lin(−)CD34(+)CD38(−) cells derived from an MDS patient.

Expression of human TIM-3 molecule in MDS patient-derived bone marrow Lin(−)CD34(+)CD38(−) cell was examined by analysis using multicolor flow cytometry. The results are shown in FIG. 9. In the patients with MDS, expression of TIM-3 was observed in all seven cases.

Figure 10:
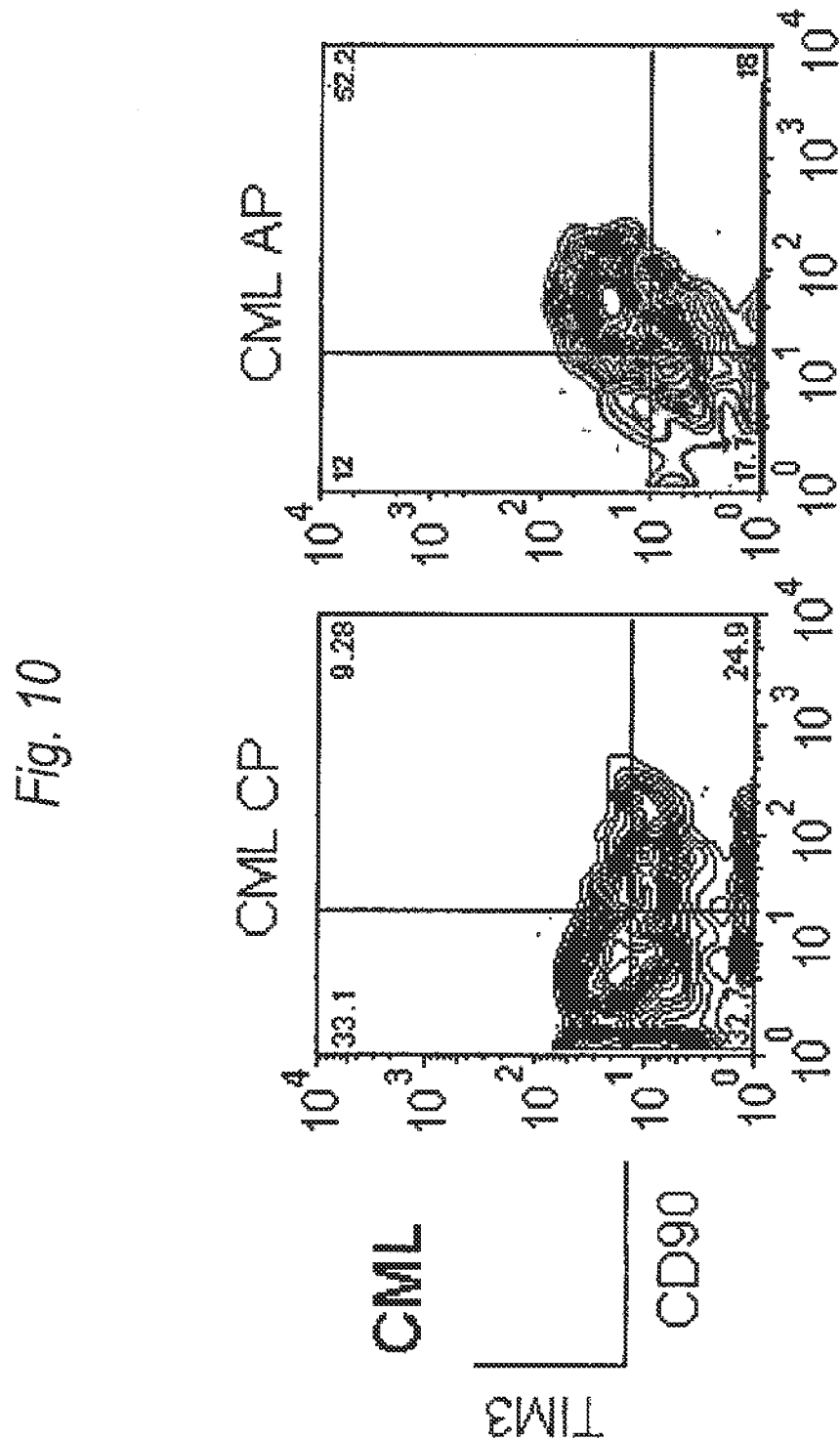
FIG. 10 shows a result of multicolor flow cytometric analysis of expression of human TIM-3 molecule on bone marrow Lin(−)CD34(+)CD38(−) cells derived from a CML patient.

Expression of human TIM-3 molecule in CML patient-derived bone marrow Lin(−)CD34(+)CD38(−) cell was examined by analysis using multicolor flow cytometry. The results are shown in FIG. 10. In the patients with CML, expression of TIM-3 was observed in all two cases.

Figure 11:
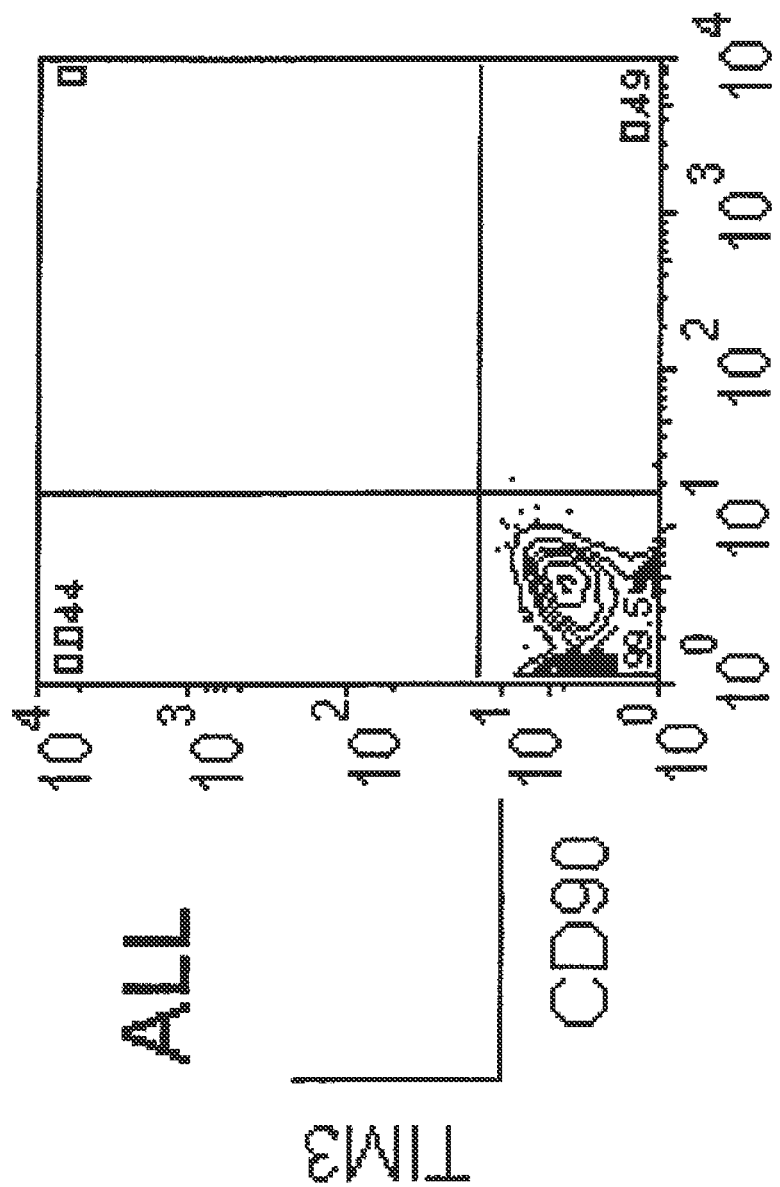
FIG. 11 shows a result of multicolor flow cytometric analysis of expression of human TIM-3 molecule on bone marrow Lin(−)CD34(+)CD38(−) cells derived from an ALL patient.

Expression of human TIM-3 molecule in ALL patient-derived bone marrow Lin(−)CD34(+)CD38(−) cell was examined by analysis using multicolor flow cytometry. The results are shown in FIG. 11. In the patient with ALL, expression of TIM-3 was not observed in one case.

Figure 12:
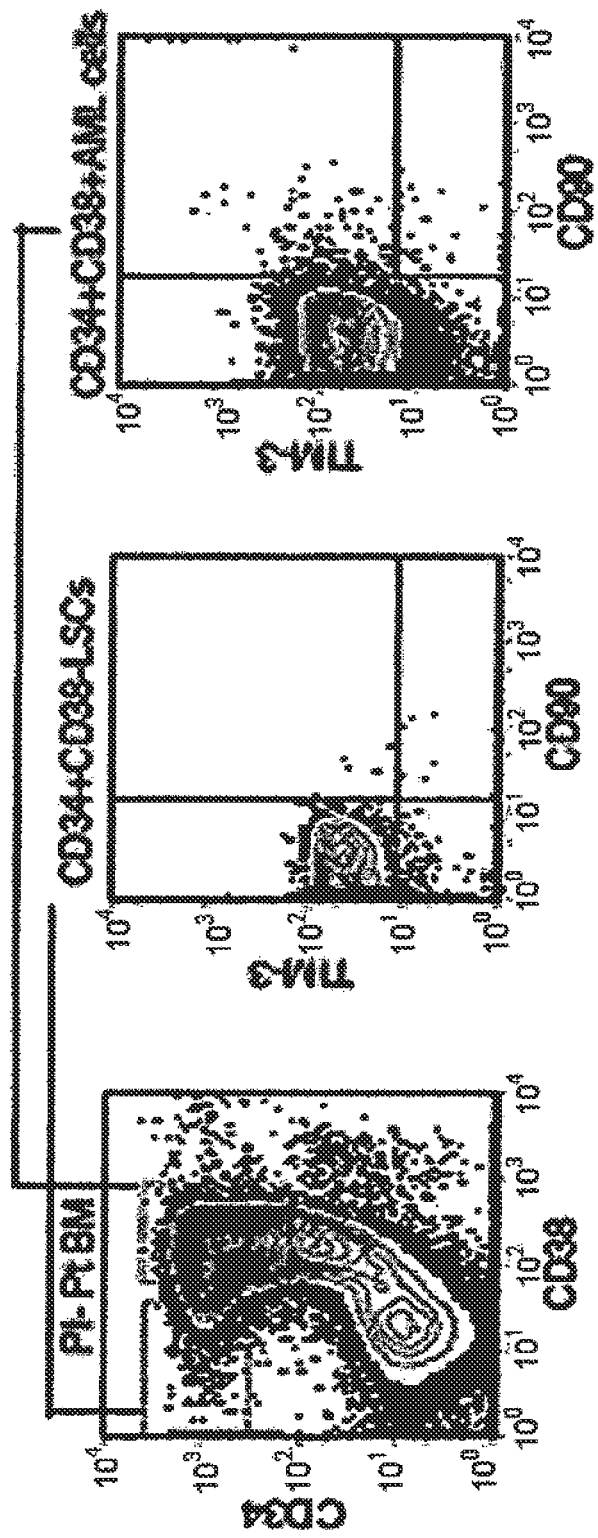
FIG. 12 shows a result of multicolor flow cytometric analysis of expression of human TIM-3 molecule on bone marrow Lin(−)CD34(+)CD38(−) cells and Lin(−) CD34(+)CD38(+) cells derived from an relapsed AML patient.

Expression of human TIM-3 molecule in bone marrow Lin(−)CD34(+)CD38(−) cell and Lin(−)CD34(+)CD38(+) cell derived from patients with recurrent AML was examined by analysis using multicolor flow cytometry. The typical results are shown in FIG. 12. In the patients with recurrent AML, expression of TIM-3 was observed in Lin(−)CD34(+)CD38(−) leukemia stem cell and Lin(−)CD34(+)CD38(+) AML cell.

Example 4

Expression of Human TIM-3 Molecule in Human Normal Blood Cells

The methods were the same as the preparation of bone marrow and peripheral blood cells in Example 1 and the staining of bone marrow normal hematopoietic and tumor stem cells and analyzing method in Example 2.

Figure 13:
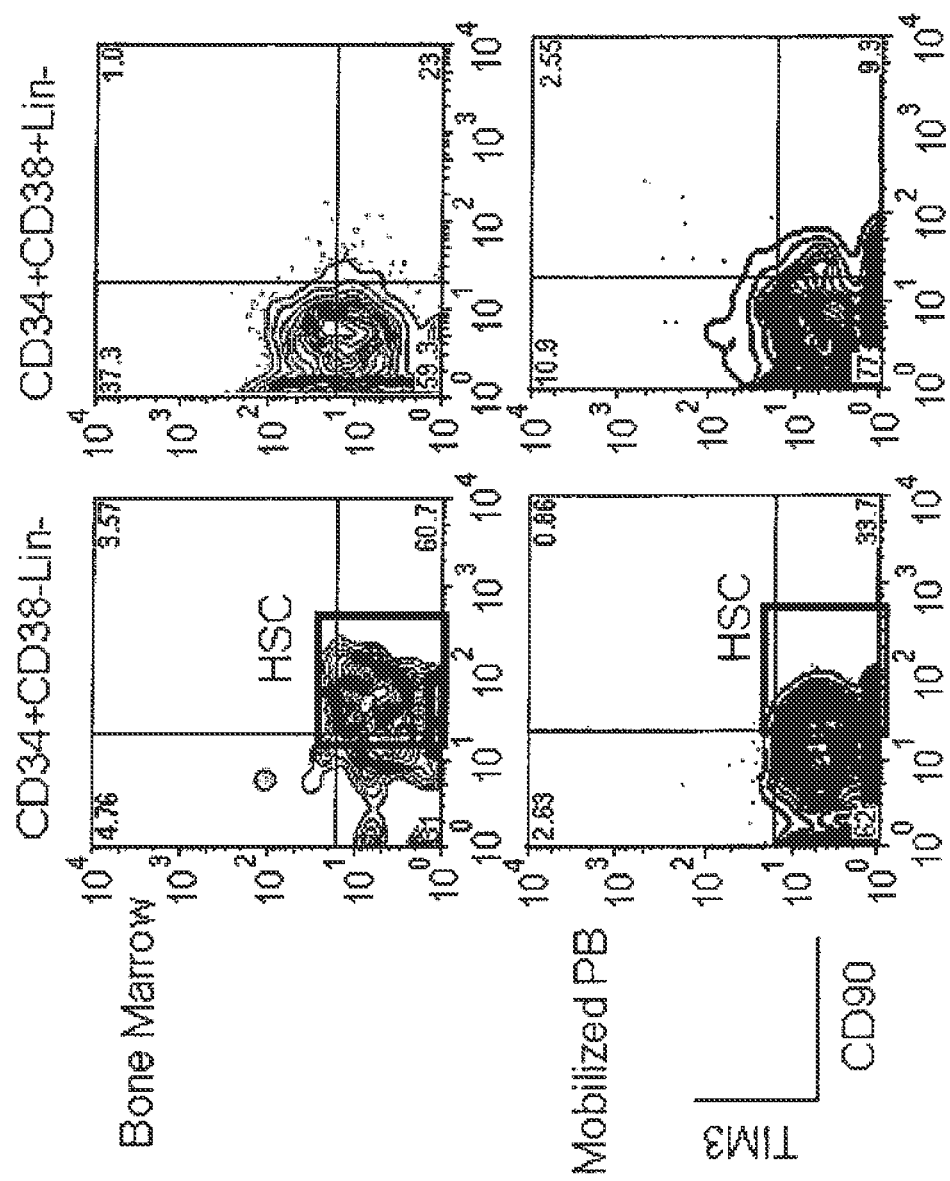
FIG. 13 shows a result of multicolor flow cytometric analysis of expression of human TIM-3 molecule on bone marrow and mobilized peripheral blood Lin(−) CD34(+)CD38(−) cells and Lin(−)CD34(+)CD38(+) cells derived from a normal healthy donors.

Expression of human TIM-3 molecule in Lin(−)CD34(+)CD38(−) cell and Lin(−)CD34(+)CD38(+) cell derived from bone marrow and mobilized peripheral blood stem cells of healthy volunteer was examined by the multicolor flow cytometry analysis. The results are shown in FIG. 13. Expression of the TIM-3 was not observed in the Lin(−)CD34(+)CD38(−)CD90(+) cell which is a normal hematopoietic stem cell fraction.

In addition, it was observed that TIM-3 was partially expressed in common lymphoid progenitor cells (CLP), common myeloid progenitor cells (CMP) and Granulocyte-Monocyte Progenitor cells (GMP), but was not expressed in Megakaryocyte-Erythroid Progenitor cells (MEP).

Expression of human TIM-3 molecule in healthy volunteer-derived normal peripheral blood cells was examined by the flow cytometry analysis. In accordance with the preparation of bone marrow and peripheral blood cells of Example 1, the cells were stained using 2 μl of anti-CD3 antibody (manufactured by BD, Cat No. 555339), 2 μl of anti-CD14 antibody (manufactured by BD, Cat No. 555413), 10 μl of anti-CD19 antibody (manufactured by BD, Cat No. 555399) and 20 μl of anti-TIM-3 antibody (manufactured by R & D Systems, 344823) at 4° C. for 40 minutes. After washing with the staining medium, the cells were re-suspended with PI-added staining medium. The analytes were analyzed by FACSAria (BD).

Figure 14:
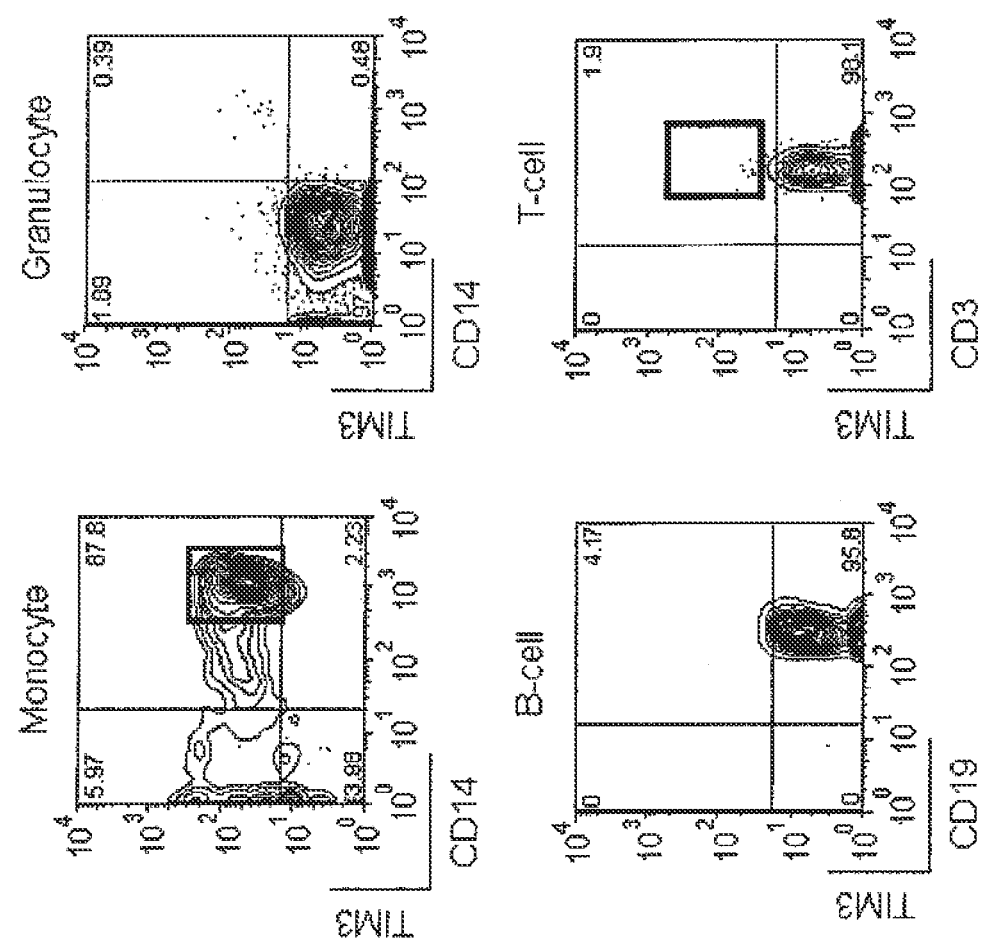
FIG. 14 shows a result of flow cytometric analysis of expression of human TIM-3 molecule on normal peripheral blood cells derived from a normal healthy person.

The results are shown in FIG. 14. Clear expression of TIM-3 was observed in the monocyte. Expression of TIM-3 was also observed in a part of the CD3 positive T cells. Its expression was not observed in the granulocytes and B cells.

Example 5

Expression of TIM-3 in Cell Lines

Expression of hTIM-3 in human cell lines was analyzed by flow cytometry

Figure 15:
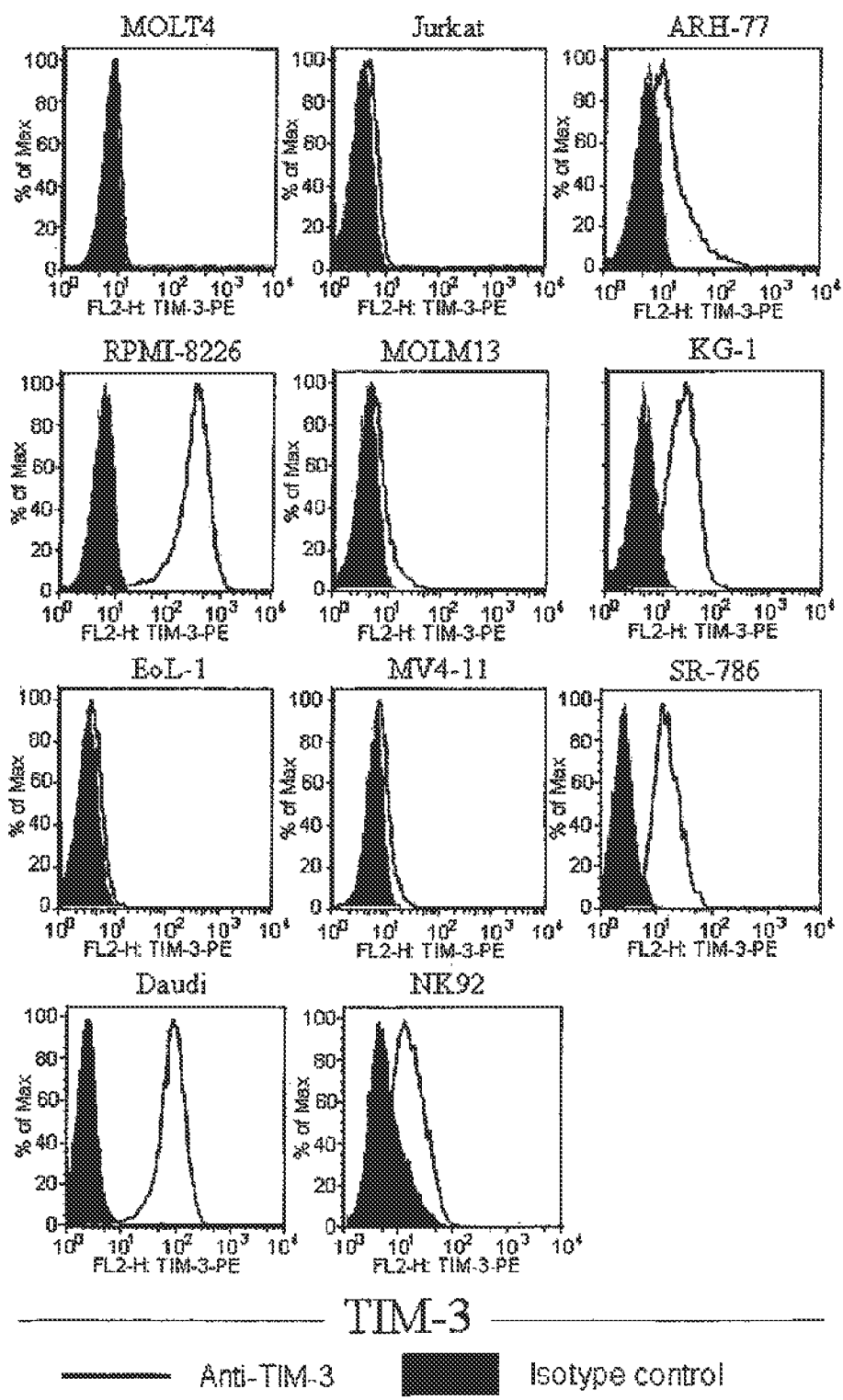
FIG. 15 shows a result of flow cytometric analysis of expression of human TIM-3 molecule on human cell lines.

The cells in culture were harvested by pipetting and concentrated by centrifugation. After washing with the staining medium, blocking was carried out using human IgG (manufactured by SIGMA, final concentration 1 mg/ml). The cells were stained with a PE-labeled anti-human TIM-3 monoclonal antibody (R & D Systems) and allowed to stand still at 4° C. for 30 minutes. After adding 7-AAD (BD Biosciences) and washing with the staining medium, the resulting cells were resuspended in the staining medium and analyzed by FACS Calibur (Becton, Dickinson and Company). The results are shown in FIG. 15. Expression of TIM-3 was observed in the Multiple Myeloma-derived RPMI-8226 cells and ARH77 cells, the B cell lymphoma-derived Daudi cells, the T cell lymphoma-derived SR-786 cells and the NK cells lymphoma-derived NK-92 cells. In addition, expression of TIM-3 was also observed in the AML-derived KG-1 cells.

For this reason, it was shown a possibility that TIM-3 was expressed in Multiple Myeloma and AML and showed that the anti-human TIM-3 antibody was useful as a therapeutic agent for these diseases.

Example 6

Preparation of Human Fc Fusion Protein of Soluble Form of Extracellular Human TIM-3 and Soluble Form of Extracellular Human TIM-3 Protein The protein is prepared according to the following method.
(Molecular Cloning of hTIM-3 cDNA)

hTIM-3 cDNA was amplified from a leukocyte-derived cDNA (CLONTECH Human MTC Panel) by PCR using ExTaq (Takara Bio Co. Ltd.). As a PCR device, GeneAmp PCR System 9700 (Applied Biosystems, hereinafter, the PCR device is the same in this specification) was used. Regarding the PCR, after a denaturation step at 95° C. for 1 minute, a three step reaction at 95° C. 15 seconds-58° C. 15 seconds-72° C. 30 seconds was carried out 40 cycles and then a reaction at 72° C. for 2 minutes was carried out. The PCR primers used were as follows.

```
TIM-3 Fw2:
                                    (SEQ ID NO: 3)
5'-GCCACCATGTTTTCACATCTTCCCTT-3'

TIM-3 Re2:
                                    (SEQ ID NO: 4)
5'-CTATGGCATTGCAAAGCGAC-3'
```

The thus obtained PCR products were subjected to 0.8% agarose gel electrophoresis (135 V, 15 minutes, TAE buffer). DNA was visualized by ethidium bromide staining. A band at around 0.9 kb was cut out and extracted using Wizard SV Gel and PCR Clean-Up System. Then 4.5 μL of the extracted DNA was mixed with 0.5 μL of pGEM-T Easy vector (Promega) and ligated using TaKaRa Ligation Kit. Regarding the transformation, the ligation sample and a DH10B competent cell were mixed and spread on LB plate (containing X-gal and ampicillin). Insert check of pGEM-T Easy vector was carried out by colony direct PCR using LA Taq (Takara Bio Co. Ltd.). Regarding the PCR, after a denaturation step at 95° C. for 1 minute, a three step reaction at 95° C. 15 seconds-56° C. 15 seconds-72° C. 30 seconds was carried out 35 cycles and then a reaction at 72° C. for 2 minutes was carried out. The primers used were as follows.

T7:
(SEQ ID NO: 5)
5'-TAATACGACTCACTATAGGG-3'

SP6:
(SEQ ID NO: 6)
5'-CATACGATTTAGGTGACACTATAG-3'

The thus obtained PCR products were subjected to 0.8% agarose gel electrophoresis (135 V, 15 minutes, TAE buffer). DNA was visualized by ethidium bromide staining. Using a colony from which amplification at around 1.2 kb was obtained, nucleotide sequence was determined by a direct sequencing method. Sequence reaction was carried out in GeneAmp PCR System 9700 (Applied Biosystems) using BigDye® Terminator v3.1 Cycle Sequencing Kit (Applied Biosystems) (hereinafter, reagent or device of the DNA sequence analysis is the same in this specification). As the PCR primers, T7 and SP6 were used. As the sequence analyzer, ABI 3700XL DNA analyzer (Applied Biosystems) was used (hereinafter, device of the DNA sequence analysis is the same in this specification). A clone which have the same sequence of the coding region of GenBank accession number NM_032782 was selected and its plasmid DNA was extracted by the Miniprep method.

(Preparation of hTIM-3 Expression Vector)

For preparation of hTIM-3 expression vector, the clone in which 5' terminal of human TIM-3 cDNA was at T7 side in cloning site of pGEM-T Easy vector. hTIM-3/GEM-T Easy plasmid DNA and pMCs-IGRetrovirus Vector (Cosmobio) were digested with NotI and subjected to 0.8% agarose gel electrophoresis (135 V, 15 minutes, TAE buffer). DNA was visualized by ethidium bromide staining. Bands around 0.9 kb and 5 kb were cut out and extracted using Wizard SV Gel and PCR Clean-Up System, respectively. Then 4.5 µL of the extracted hTIM-3 DNA was mixed with 0.5 µL of pMCs-IGvector DNA and ligated using TaKaRa Ligation Kit. Regarding the transformation, the ligation sample and a DH10B competent cell were mixed and spread on LB plate (containing ampicillin). Insert check was carried out by colony direct PCR using LA Taq (Takara Bio Co. Ltd.). Regarding the PCR, after a denaturation step at 95° C. for 1 minute, a three step reaction at 95° C. 15 seconds-56° C. 15 seconds-72° C. 45 seconds was carried out 35 cycles and then a reaction at 72° C. for 2 minutes was carried out.

The primers used were as follows.

pMCs-Fw:
(SEQ ID NO: 7)
5'-TCAAAGTAGACGGCATCGCAG-3'

TIM-3 Re1:
(SEQ ID NO: 8)
5'-GCATTGCAAAGCGACAAC-3'

The thus obtained PCR products were subjected to 0.8% agarose gel electrophoresis (135 V, 15 minutes, TAE buffer). DNA was visualized by ethidium bromide staining. From a colony in which amplification at around 1.1 kb was obtained, the plasmid DNA was extracted using Miniprep method. The purified hTIM-3/pMCs-IG plasmid DNA was found to have the same sequence of the coding region of GenBank accession number NM_032782 by DNA sequence analysis. The primers used for DNA sequence analysis were as follows.

pMCs-Fw:
(SEQ ID NO: 9)
5'-TCAAAGTAGACGGCATCGCAG-3' hTIM-3 Fw1:
(SEQ ID NO: 10)
5'-ACTCTGGAGCAACCATCA-3'

In order to confirm the expression of hTIM-3 protein, hTIM-3/pMCs-IG plasmid DNA was expressed transiently in 293T cells. FuGene6 (Roche) was used for transfection. Two days after, 293T cells were harvested and then washed with a staining medium (PBS containing 2% FCS and 0.05% NaN$_3$) and stained with PE-labeled anti-human TIM-3 monoclonal antibody (R&D System). After washing with the staining medium, 7-AAD (BD Biosciences) was added and then the obtained cells were analyzed with FACS Calibur (Becton, Dickinson and Company). As a result, expression of hTIM-3 protein from hTIM-3/pMCs-IG vector was confirmed.

(Preparation of hTIM-3 Stable Expression Cell)

hTIM-3/pMCs-IG or EmptypMCs-IG and VSV-G expression vectors were introduced into 293gp cells. FuGene6 (Roche) was used for transfection. Three days after, the culture supernatant was harvested and contaminants were removed using 0.45 µm filter (Milipore). After centrifugation (6000×g, 4° C. for 7 hours), the precipitate was dissolved with IMDM medium (Invitrogen). The concentrated retrovirus solution and Protamine solution (Wako Pure Chemical Industries, Ltd., final concentration: 100 µg/ml) were added to the medium of EoL-1 cells and Jarkat cells. After several passages, GFP positive infected cells in the culture medium were sorted and collected by FACSAria. After further several passages, GFP positive infected cells in the culture medium were sorted and collected again by FACSAria. After several passages, the expression of TIM-3 was confirmed by a flow cytometry method using PE-labeled anti-TIM-3 monoclonal antibody.

(Preparation of Expression Vector of Fusion Protein of Human Fc Protein and Soluble Form of Extracellular Human TIM-3)

A cDNA encoding the extracellular region of human TIM-3 was amplified by using a PCR method and FLAG tag and human Fc sequence were fused to its downstream (sTIM-3-FLAG-Fc/pTracerCMV).

The cDNA encoding the extracellular region of human TIM-3 was amplified by using a PCR method using hTIM-3/pMCs-IG plasmid as a template and PrimeSTAR® HS DNA Polymerase (Takara Bio Co. Ltd.). Regarding the PCR, a two step reaction at 98° C. 10 seconds-68° C. 40 seconds was carried out 20 cycles. The primers used were as follows.

pMCs-Fw:
(SEQ ID NO: 11)
5'-TCAAAGTAGACGGCATCGCAG-3'

TIM3ED-FcReXba:
(SEQ ID NO: 12)
5'-TTTTCTAGATCTGATGGTTGCTCCAGA-3'

The thus obtained PCR products were subjected to 0.8% agarose gel electrophoresis (135 V, 15 minutes, TAE buffer). DNA was visualized by ethidium bromide staining. A band of around 0.6 kb was cut out and the DNA was extracted using Wizard SV Gel and PCR Clean-Up System. Thus purified DNA was digested with EcoRI and XbaI and subjected to 0.8% agarose gel electrophoresis (135 V, 15 minutes, TAE buffer). A band of around 0.9 kb was cut out and the DNA was extracted using Wizard SV Gel and PCR Clean-Up System. The obtained DNA was mixed with a pTracer-CMV-FLAG-humanFc vector (a plasmid in which FLAG and Fc region of human IgG were inserted between XbaI site and ApaI site of the modified pTracer-CMV [manufactured by Invitrogen]), which had been cleaved using the same enzymes of the purified DNA, and ligated using TaKaRa Ligation Kit. Regarding the transformation, the ligation sample and a DH10B competent cell were mixed and spread on LB plate (containing ampicillin). Insert check was carried out by colony direct PCR using LA Taq (Takara Bio Co. Ltd.). Regarding the PCR, after a denaturation step at 95° C. for 1 minute, a three step reaction at 95° C. 15 seconds-56° C. 15 seconds-72° C. 40 seconds was carried out 35 cycles and then a reaction at 72° C. for 2 minutes was carried out. The primers used were as follows.

T7:
(SEQ ID NO: 13)
5'-TAATACGACTCACTATAGGG-3'

TIM3ED-FcReXba:
(SEQ ID NO: 14)
5'-TTTTCTAGATCTGATGGTTGCTCCAGA-3'

The thus obtained PCR products were subjected to 0.8% agarose gel electrophoresis (135 V, 15 minutes, TAE buffer). DNA was visualized by ethidium bromide staining. A plasmid DNA was extracted by the Miniprep method from a colony in which amplification of around 0.7 kb was obtained. It was found by a DNA sequence analysis that the purified TIM-3-FLAG-Fc/pTracerCMV plasmid DNA had the sequence identical to the corresponding region of GenBank accession number NM_032782. The primers used for the DNA sequence analysis were as follows.

T7:
(SEQ ID NO: 15)
5'-TAATACGACTCACTATAGGG-3' hTIM-3 Fw1:
(SEQ ID NO: 16)
5'-ACTCTGGAGCAACCATCA-3'

The sequence of the insert (from the following EcoRI recognition site to just before ApaI recognition site) was as follows.

(SEQ ID NO: 17)
GATTGCCACCATGTTTTCACATCTTCCCTTTGACTGTGTCCTGCTGCTG

CTGCTGCTACTACTTACAAGGTCCTCAGAAGTGGAATACAGAGCGGAGG

TCGGTCAGAATGCCTATCTGCCCTGCTTCTACACCCCAGCCGCCCCAGG

GAACCTCGTGCCCGTCTGCTGGGGCAAAGGAGCCTGTCCTGTGTTTGAA

TGTGGCAACGTGGTGCTCAGGACTGATGAAAGGGATGTGAATTATTGGA

CATCCAGATACTGGCTAAATGGGGATTTCCGCAAAGGAGATGTGTCCCT

GACCATAGAGAATGTGACTCTAGCAGACAGTGGGATCTACTGCTGCCGG

ATCCAAATCCCAGGCATAATGAATGATGAAAAATTTAACCTGAAGTTGG

TCATCAAACCAGCCAAGGTCACCCCTGCACCGACTCGGCAGAGAGACTT

CACTGCAGCCTTTTCCAAGGATGCTTACCACCAGGGGACATGGCCCAGCA

GAGACACAGACACTGGGGAGCCTCCCTGATATAAATCTAACACAAATAT

CCACATTGGCCAATGAGTTACGGGACTCTAGATTGGCCAATGACTTACG

GGACTCTGGAGCAACCATCAGATCTAGAGCAGACTACAAGGACGACGAT

GACAAGACTAGTGACAAAACTCACACATGCCCACCGTGCCCAGCACCTG

AACTCCTGGGGGGACCGTCAGTCTTCCTCTTCCCCCCAAAACCCAAGGA

CACCCTCATGATCTCCCGGACCCCTGAGGTCACATGCGTGGTGGTGGAC

GTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTG

AATGGCAAGGAGTACAAGTGCAAGGTCTCCAACAAAGCCCTCCCAGCCC

CCATCGAGAAAACCATCTCCAAAGCCAAAGGGCAGCCCCGAGAACCACA

GGTGTACACCCTGCCCCCATCCCGGGAGGAGATGACCAAGAACCAGGTC

AGCCTGACCTGCCTGGTCAAAGGCTTCTATCCCAGCGACATCGCCGCGG

AGTGGGAGAGCAATGGGCAGCCGGAGAACAACTACAAGACCACGCCTCC

CGTGCTGGACTCCGACGGCTCCTTCTTCCTCTACAGCAAGCTCACCGTG

GACAAGAGCAGGTGGCAGCAGGGGAACGTCTTCTCATGCTCCGTGATGC

ATGAGGCTCTGCACAACCACTACACGCAGAAGAGCCTCTCCCTGTCTCC

GGGTAAATGATGA (Preparation of Expression Vector of Soluble Form of Extracellular Region of Human TIM-3)

A cDNA encoding the extracellular region of human TIM-3 was amplified by using a PCR method, and FLAG tag was connected to its downstream (sTIM-3-FLAG/pEF6 Myc_HisC).

The cDNA encoding the extracellular region of human TIM-3 was amplified by using a PCR method using hTIM-3/pGEM-T Easy plasmid as a template and PrimeSTAR® HS DNA Polymerase (Takara Bio Co. Ltd.). Regarding the PCR, a two step reaction at 98° C. 10 seconds-68° C. 30 seconds was carried out 25 cycles. The primers used were as follows.

TIM-3 Fw2:
(SEQ ID NO: 18)
5'-GCCACCATGTTTTCACATCTTCCCTT-3'

TIM3ED-FLAG4aa:
(SEQ ID NO: 19)
5'-GTCCTTGTAGTCTCTGATGGTTGCTCCAGA-3'

Using 2 µL of the obtained PCR product as a template, the DNA was amplified by using LA taq (Takara Bio Co. Ltd.) by a PCR method. Regarding the PCR, after a denaturation step at 95° C. for 1 minute, a three step reaction at 95° C. 15 seconds-58° C. 15 seconds-72° C. 30 seconds and then a reaction at 72° C. for 2 minutes was carried out 16 cycles. The primers used were as follows.

TIM-3 Fw2:
(SEQ ID NO: 20)
5'-GCCACCATGTTTTCACATCTTCCCTT-3'

C-FLAG-NotR2:
(SEQ ID NO: 21)
5'-AAAAGCGGCCGCTCACTTGTCGTCATCGTCCTTGTAGTC-3'

The thus obtained PCR products were subjected to 0.8% agarose gel electrophoresis (135 V, 15 minutes, TAE buffer).

DNA was visualized by ethidium bromide staining. A band at around 0.6 kb was cut out and extracted using Wizard SV Gel and PCR Clean-Up System. Then 4 µL of the extracted DNA was mixed with 0.5 µL of pGEM-T Easy vector (Promega) and ligated using Quick Ligation™ Kit (New England Biolabs). Regarding the transformation, the ligation sample and a DH10B competent cell were mixed and spread on LB plate (containing X-gal and ampicillin). Insert check of pGEM-T Easy vector was carried out by colony direct PCR using LA Taq (Takara Bio Co. Ltd.). Insert check of pGEM-T Easy vector was carried out by colony direct PCR using LA Taq (Takara Bio Co. Ltd.). Regarding the PCR, after a denaturation step at 95° C. for 1 minute, a three step reaction at 95° C. 15 seconds-56° C. 15 seconds-72° C. 30 seconds was carried out 38 cycles and then a reaction at 72° C. for 2 minutes was carried out. The primers used were as follows.

```
T7:
                                         (SEQ ID NO: 22)
5'-TAATACGACTCACTATAGGG-3'

SP6:
                                         (SEQ ID NO: 23)
5'-CATACGATTTAGGTGACACTATAG-3'
```

The thus obtained PCR products were subjected to 0.8% agarose gel electrophoresis (135 V, 15 minutes, TAE buffer). DNA was visualized by ethidium bromide staining. Using a colony from which amplification at around 0.8 kb was obtained, nucleotide sequence was determined by a direct sequencing method. As the PCR primers, T7 and SP6 were used. A clone containing the same sequence of the coding region of GenBank accession number NM_032782 and its plasmid DNA was extracted by the Miniprep method.

For preparation of the expression vector for expressing soluble form of extracellular region of human TIM-3, the clone in which 5' terminal of human TIM-3 cDNA was at T7 side in cloning site of pGEM-T Easy vector. hTIM-3/GEM-T Easy plasmid DNA and pEF6Myc_HisC (Invitrogen) were digested with NotI and subjected to 0.8% agarose gel electrophoresis (135 V, 15 minutes, TAE buffer). DNA was visualized by ethidium bromide staining. Bands around 0.6 kb and 5 kb were cut out and extracted using Wizard SV Gel and PCR Clean-Up System, respectively. Then 4 µL of the extracted sTIM-3 cDNA was mixed with 0.5 µL of pEF6 Myc_HisC vector DNA, and ligated using QuickLigation™ Kit (New England Biolabs). Regarding the transformation, the ligation sample and a DH10B competent cell were mixed and spread on LB plate (containing ampicillin). Insert check was carried out by colony direct PCR using LA Taq (Takara Bio Co. Ltd.). Regarding the PCR, after a denaturation step at 95° C. for 1 minute, a three step reaction at 95° C. 15 seconds-56° C. 15 seconds-72° C. 60 seconds was carried out 38 cycles and then a reaction at 72° C. for 2 minutes was carried out. The primers used were as follows.

```
TIM-3 Fw2:
                                         (SEQ ID NO: 24)
5'-GCCACCATGTTTTCACATCTTCCCTT-3'

BGH-R:
                                         (SEQ ID NO: 25)
5'-TAGAAGGCACAGTCGAGG-3'
```

From a colony in which amplification at around 0.8 kb was obtained, the plasmid DNA was extracted using Miniprep method.

It was confirmed by a DNA sequence analysis that the purified sTIM-3-FLAG/pEF6 Myc_HisC plasmid DNA had the sequence identical to the corresponding region of GenBank accession number NM_032782. The primers used for the DNA sequence analysis were as follows.

```
T7:
                                         (SEQ ID NO: 26)
5'-TAATACGACTCACTATAGGG-3'

BGH-R:
                                         (SEQ ID NO: 27)
5'-TAGAAGGCACAGTCGAGG-3'
```

The sequence of the insert (from the following NotI recognition site to just before NotI recognition site) was as follows.

```
                                         (SEQ ID NO: 28)
GGGAATTCGATTGCCACCATGTTTTCACATCTTCCCTTTGACTGTGTC

CTGCTGCTGCTGCTGCTACTACTTACAAGGTCCTCAGAAGTGGAATAC

AGAGCGGAGGTCGGTCAGAATGCCTATCTGCCCTGCTTCTACACCCCA

GCCGCCCCAGGGAACCTCGTGCCCGTCTGCTGGGGCAAAGGAGCCTGT

CCTGTGTTTGAATGTGGCAACGTGGTGCTCAGGACTGATGAAAGGGAT

GTGAATTATTGGACATCCAGATACTGGCTAAATGGGGATTTCCGCAAA

GGAGATGTGTCCCTGACCATAGAGAATGTGACTCTAGCAGACAGTGGG

ATCTACTGCTGCCGGATCCAAATCCCAGGCATAATGAATGATGAAAAA

TTTAACCTGAAGTTGGTCATCAAACCAGCCAAGGTCACCCCTGCACCG

ACTCGGCAGAGAGACTTCACTGCAGCCTTTCCAAGGATGCTTACCACC

AGGGGACATGGCCCAGCAGAGACACAGACACTGGGGAGCCTCCCTGAT

ATAAATCTAACACAAATATCCACATTGGCCAATGAGTTACGGGACTCT

AGATTGGCCAATGACTTACGGGACTCTGGAGCAACCATCAGAGACTAC

AAGGACGATGACGACAAGTGA
```

(Preparation of Fusion Protein of Human Fc and Soluble Form of Extracellular Human TIM-3 and, Soluble Form of Extracellular Human TIM-3)

Plasmid DNAs of sTIM-3-FLAG-Fc/pTracerCMV and sTIM-3-FLAG/pEF6 Myc_HisC were purified using QIAGEN Plasmid Maxi Kit.

HEK293F cells were used as a host cell for expression. The HEK293F cells were cultured with shaking in FreeStyle 293 Expression Medium (Invitrogen) (37° C., 5% $CO_2$).

The PEI method was used in the gene introduction. Polyethylenimine (Linear, MW 25,000, manufactured by Polysciences) was weighed and dissolved in PBS (1 g/l) while adjusting to around pH 7.0 with HCl. The obtained solution was stirred for 1 hour and then sterilized by filtering through a membrane filter having a pore size of 0.22 µm, MILLEX-GV (Millipore). Then, 1 mg of the purified plasmid DNA was mixed with 20 ml of Opti-Pro SFM (Invitrogen) to obtain Solution A. Solution B was prepared by mixing 2.5 ml of PEI solution (1 g/l) with 20 ml of Opti-Pro SFM (Invitrogen). After solution A and Solution B were mixed and allowed to stand still for 10 minutes, and then the obtained solution was added to 1 L of 293F cells (1,000,000 cells per 1 ml). After six days, the cell supernatant was harvested and used for the protein purification.

Purification of the fusion protein of human Fc and soluble form of extracellular human TIM-3 and the soluble form of human TIM-3 protein were carried out by the following method. The culture supernatant containing the fusion protein of human Fc and soluble form of extracellular human TIM-3 and the soluble form of TIM-3 protein were harvested by centrifugation 6 days after the transfection and passed through a filter (950 ml). The obtained solution was diluted 5-fold with Tris buffered saline (TBS), an anti-FLAG column was prepared using anti-FLAG M2 Agarose Affinity Gel (Sigma) and the solution was applied thereto using HiLoad Pump P-50 (Pharmacia Biotech). Elution was carried out using FLAG peptide (Sigma) in accordance with the manual. The eluate was fractionated into 8 fractions, each fraction was subjected to SDS-PAGE (MultiGel II Mini 10/20% gradient gel; Cosmo Bio Co., Ltd.) under a reducing condition, and then silver staining and Western blotting were carried out. A silver staining reagent "Daiichi" (Daiichi Pure Chemicals Co., Ltd.) was used for the silver staining. Anti-FLAG M2 antibody (Sigma) and an alkaline phosphatase-labeled rabbit anti-mouse immunoglobulin antibody were used for the Western blotting. Fractions in which the protein of interest was found were concentrated using Amicon Ultra-4 10K (Millipore), and gel filtration chromatography was carried out using Superdex 200 gp (GE Healthcare). After fractionation, each fraction was subjected to SDS-PAGE (MultiGel II Mini 10/20% gradient gel; Cosmo Bio Co., Ltd.) under a reducing condition, and then silver staining and Western blotting were carried out. A silver staining reagent "Daiichi" (Daiichi Pure Chemicals Co., Ltd.) was used in the silver staining. Anti-FLAG M2 antibody (Sigma) and an alkaline phosphatase-labeled rabbit anti-mouse immunoglobulin antibody were used in the Western blotting. Fractions in which the protein of interest was found were concentrated using Amicon Ultra-4 10K (Millipore) and washed with PBS. By carrying out sterilization by filtration using a membrane filter MILLEX-GV (Millipore) having a pore size of 0.22 µm, a fusion protein of human Fc and soluble form of extracellular human TIM-3, and soluble form of extracellular human TIM-3 were obtained. As a result of Limulus test using Limulus ES-II Kit Wako (Wako Pure Chemical Industries, Ltd.), endotoxin was not detected in the fusion protein of human Fc and soluble form of extracellular human TIM-3, and the soluble form of extracellular human TIM-3. Regarding concentration of the in the fusion protein of human Fc and soluble form of extracellular human TIM-3, and the soluble form of extracellular human TIM-3, absorbance at 280 nm was measured and 1 mg/ml was calculated as 1.4 OD.

Example 7

Cytotoxicity Test of TIM-3 Expressing Cell Line Using Anti-TIM-3 Polyclonal Antibody Regarding the cellular cytotoxicity mediated by an antibody, cytotoxicity for target cells (Antibody-Dependent Cellular Cytotoxicity, hereinafter ADCC) was measured in the presence of an antibody using human peripheral blood-derived mononuclear cells (hereinafter PBMCs) as an effector.

Goat-derived anti-TIM-3 polyclonal antibody (R & D Systems; AF2365) was used as an antibody. In addition, goat-derived IgG (manufactured by SIGMA; 15256-10MG) was used as a negative control.

Regarding the method, briefly, a target cells are cultured in the presence of PBMCs and lysis of the target cells by an antibody is measured.

Specifically, as a target cell, each of TIM-3-transfected Jurkat cells and a TIM-3-transfected EoL-1 cells were cultured with sodium chromate labeled with a radioisotope $^{51}$Cr (Na$_2$$^{51}$CrO$_4$, manufactured by PerkinElmer Corp., NEZ030S) at 37° C. for 1 hour in the presence of 5% CO$_2$ to label the target cell with $^{51}$Cr. After the labeled target cells were washed three times with RPMI-1640 medium containing 10% FCS to remove excess $^{51}$Cr, the cells were suspended in the medium (40,000 cells/ml) and then dispensed in 50 µl/well into a 96-well plate. PBMCs were suspended in the medium (4,000,000 cells/ml) and dispensed in 50 µl/well into the plate (effector/target ratio=100). An antibody was suspended in the medium and 50 µl of the obtained suspension was added to the plate (final concentration 10 µg/ml) to culture at 37° C. for 4 hours in the presence of 5% CO$_2$. As the antibody, anti-human TIM-3 goat polyclonal antibody (manufactured by R & D Systems) was used, and goat IgG (manufactured by SIGMA) was used as the negative control. The PBMCs, using as the effector, were derived from healthy human peripheral blood.

Regarding the lysis rate of target cells, amount of $^{51}$Cr in the sodium chromate released into the medium due to the lysis of cells was measured. That is, after the plate was centrifuged, the supernatant was transferred in 50 µl portions into a scintillator-coated 96-well plate (Lumaplate-™, manufactured by Perkin-Elmer Corp.) and then dried at 56° C. for 2 hours. The plate was sealed (TopSeal-A, manufactured by Packard Instrument Co., Inc.) and measured using a microplate reader (TopCount, manufactured by Perkin-Elmer Corp.).

Figure 16:
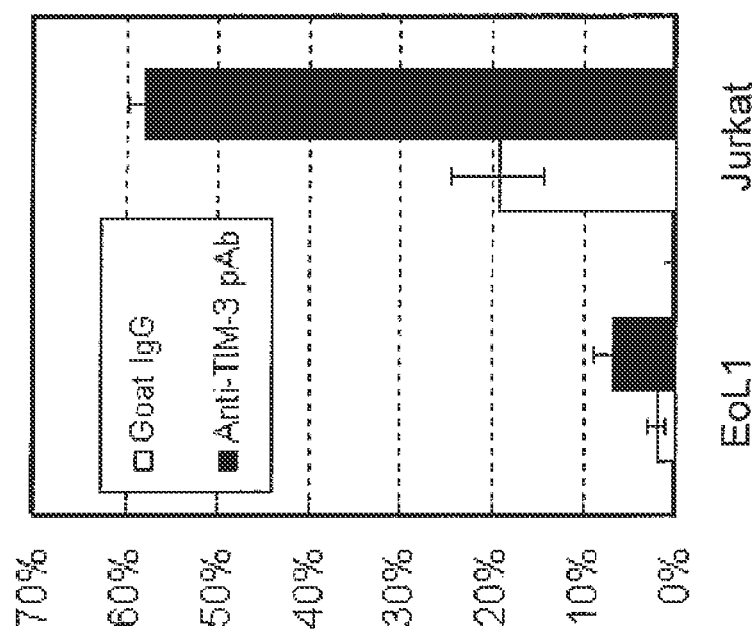
FIG. 16 shows a result of ADCC assay of AML cell line using anti-TIM-3 polyclonal antibody. The ordinate shows specific lysis rate.

The results are shown in FIG. 16. Regarding the significance test, by comparing with the goat IgG using the standard Student's t-test, those having a level of significance (p) of 0.05 or less was considered to be significantly different.

In comparison with the human-derived IgG control, it was found that the anti-TIM-3 polyclonal antibody exhibited significant increase lysis rate of the target cell as shown below. For this reason, the anti-TIM-3 polyclonal antibody was shown to have the ADCC on TIM-3 expression cells. Accordingly, the example showed a possibility of treatment in which removal of TIM-3 positive cells using ADCC could be drug efficacy.

In addition, as cytotoxicity on target cells, Complement-Dependent Cytotoxicity (hereinafter CDC) was measured in the presence of complement and an antibody.

Regarding the method, briefly, radioactive chrome ($^{51}$Cr) was incorporated into the cytoplasm of target cells and then the amount of $^{51}$Cr released into culture medium by cell death was measured as the amount of γ ray.

Specifically, 10$^6$ cells of the TIM-3-transfected EoL-1 cell or TIM-3-transfected Jurkat cell as a target cells were suspended in 15 µl of Fetal Calf Serum (FCS), mixed with 50 µl (37 MBq/ml) of $^{51}$Cr-labeled sodium chromate (manufactured by Perkin-Elmer Corp., hereinafter referred to as $^{51}$Cr) and cultured at 37° C. for 1 hour. Next, $^{51}$Cr which was not incorporated into the cells was removed by repeating the step, consisting of adding 10 ml of the medium, centrifugation and discarding the medium, three times.

Regarding CDC, 2000 cells of the $^{51}$Cr-labeled TIM-3-transfected EoL-1 cell were mixed with 25% in final concentration of baby rabbit serum-derived complement (manufactured by Cedarlane; CL3441) and the antibody having each concentration (0 µg/ml, 0.01 µg/ml, 0.1 µg/ml, 1 µg/ml or 10 µg/ml in final concentration). In a U bottom 96-well plate, total volume of the mixed liquid was adjusted to 150 µl and cultured at 37° C. for 2 hours in the presence of 5%

$CO_2$. In addition, 0.33% in final concentration of Triton-X100 was added thereto as a control. After culturing, the plate was centrifuged so as to precipitate the cells. Fifty μl of the supernatant was transferred into a powder scintillator-containing 96-well plate (Lumaplate™-96: manufactured by Packard Instrument Co., Inc.), and the plate was dried at 56° C. for 2 hours. After confirmation of drying, the plate was sealed (TopSeal™-A: 96-well Microplates: manufactured by Packard Instrument Co., Inc.) and the amount of γ ray was measured using a scintillation counter (TopCount, manufactured by Packard Instrument Co., Inc.).

A specific lysis rate was calculated by dividing a value obtained by subtracting the γ ray dosage at an antibody concentration of 0 μg/ml from the value of each well, by the value of the well to which Triton-X100 was added (specific lysis rate is regarded as 100%). The results are shown in FIG. 17. It was found that TIM-3 polyclonal antibody exhibited cytotoxicity on target cells in concentration-dependent manner. Accordingly, the example showed a possibility of treatment in which removal of TIM-3 positive cells using CDC would be drug efficacy.

Example 8

AML Primary Cell Toxicity Test by Anti-TIM-3 Polyclonal Antibody

Regarding the cytotoxicity mediated by an antibody, as cytotoxicity on target cells, complement-dependent cytotoxicity (hereinafter CDC) was measured in the presence of complement and an antibody.

Regarding the method, briefly, target cells are cultured in the presence of a complement and the decrease of the cell viability due to the antibody is measured.

As an antibody, goat-derived anti-TIM-3 polyclonal antibody was used, and as an antibody of negative control, goat-derived IgG (manufactured by SIGMA; 15256-10MG) was used.

Specifically, primary AML cells from a patient as target cells were suspended in RPMI-1640 medium containing 10% FCS and 1,000,000 cells/well were dispensed into a 24-well plate (462.5 μl/well). To the cell, 12.5 μl/well (2.5% in final concentration) of baby rabbit serum-derived complement (manufactured by Cedarlane; CL3441) was added. After 25 μl of goat-derived anti-TIM-3 polyclonal antibody (0.2 mg/ml) was added (10 μg/ml in final concentration), the cells were cultured at 37° C. for 3 hours in the presence of 5% $CO_2$.

Ratio of dead cells was evaluated by flow cytometry by AnnexinV staining. After washing with PBS, the cells were suspended in 50 μl of AnnexinV Binding Buffer (manufactured by BD) again, and stained at room temperature for 10 minutes by adding PI and AnnexinV-FITC (manufactured by BD). After diluting with 200 μl of AnnexinV Binding Buffer (manufactured by BD), the sample was analyzed by FACSAria (manufactured by BD). The ratio of the AnnexinV(+) PI(−) cells and PI(+) cells in the entire AML cells was regarded as the ratio of dead cells.

Figure 8:
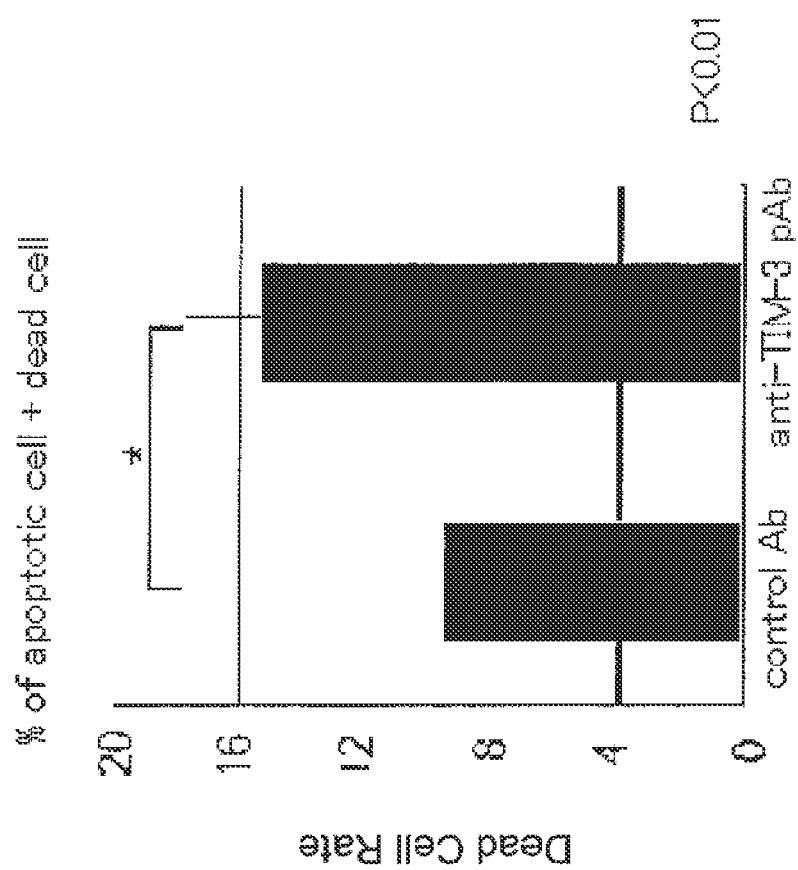
FIG. 8 shows a result of cytotoxic assay for AML primary cells using an anti-TIM-3 polyclonal antibody.

The results are shown in FIG. 8. Regarding the significance test, by comparing with the human-derived IgG using the standard Student's t-test, those having a level of significance (p) of 0.05 or less was considered to be significantly different.

In comparison with the human-derived IgG control, significant increase in the ratio of dead to live cells was found in the anti-TIM-3 polyclonal antibody. For this reason, it was shown that the antibody had CDC on TIM-3 positive primary AML cells. Accordingly, the example showed a possibility of treatment in which removal of primary AML cells would be drug efficacy.

INDUSTRIAL APPLICABILITY

The invention can provide a method for treatment comprising administering anti-TIM-3 antibody to a subject which is a candidate of blood tumor in which TIM-3 is expressed in Lin(−)CD34(+)CD38(−) cell fraction of bone marrow or peripheral blood or a subject who has received treatment for blood tumor.

FREE TEXT OF SEQUENCE LISTING

SEQ ID NO:3: TIM-3Fw2 primer
SEQ ID NO:4: TIM-3 Re2 primer
SEQ ID NO:5: T7 primer
SEQ ID NO:6: SP6 primer
SEQ ID NO:7: pMCs-Fw primer
SEQ ID NO:8: TIM-3 Re1 primer
SEQ ID NO:9: pMCs-Fw primer
SEQ ID NO:10: hTIM-3 Fw1 primer
SEQ ID NO:11: pMCs-Fw primer
SEQ ID NO:12: TIM3ED-FcReXba primer
SEQ ID NO:13: T7 primer
SEQ ID NO:14: TIM3ED-FcReXba primer
SEQ ID NO:15: T7 primer
SEQ ID NO:16: hTIM-3 Fw1 primer
SEQ ID NO:17: Insert (from the following EcoRI recognition site just prior to ApaI recognition site)
SEQ ID NO:18: TIM-3Fw2 primer
SEQ ID NO:19: TIM3ED-FLAG4aa primer
SEQ ID NO:20: TIM-3 Fw2 primer
SEQ ID NO:21: C-FLAG-NotR2 primer
SEQ ID NO:22: T7 primer
SEQ ID NO:23: SP6 primer
SEQ ID NO:24: TIM-3 Fw2 primer
SEQ ID NO:25: BGH-R primer
SEQ ID NO:26: T7 primer
SEQ ID NO:27: BGH-R primer
SEQ ID NO:28: Insert (from the following NotI recognition site just prior to NotI recognition site)

What is claimed is:

1. A method for treating a tumor in a subject, comprising administering an anti-T-cell immunoglobulin and mucin-domain containing-3 (TIM-3) antibody or its TIM-3 binding fragment to the subject who is suspected to have a tumor in which a cell expressing TIM-3 is recognized in bone marrow or peripheral blood, wherein the cell is at least one cell fraction of
  (a) Lin(−)CD34(+)CD38(+) or
  (b) Lin(−)CD34(−).

2. The method according to claim 1, wherein the tumor is lymphoma, myelodysplastic syndromes, acute myeloid leukemia or chronic myeloid leukemia.

3. The method according to claim 1, wherein the blood tumor is recurrence and/or refractory.

4. The method according to claim 1, wherein the anti-TIM-3 antibody is an antibody which has a constant region originated from a human species.

5. The method according to claim 1, wherein the anti-TIM-3 antibody is at least one antibody selected from the group consisting of a monoclonal antibody, a chimeric antibody, a humanized antibody and a human antibody.

6. The method according to claim 1, wherein the anti-TIM-3 monoclonal antibody is an antibody having ADCC activity and/or CDC activity.

7. A method for decreasing a tumor in a subject comprising administering an anti-T-cell immunoglobulin and mucin-domain containing-3 (TIM-3) antibody or its TIM-3 binding fragment to the subject who is suspected to have tumor in which a cell expressing TIM-3 is recognized in bone marrow or peripheral blood, wherein the tumor is recurrence and/or refractory.

8. The method according to claim 7, wherein the cell is at least one cell fraction selected from the group consisting of (a) to (c):
  (a) Lin(−)CD34(+)CD38(−),
  (b) Lin(−)CD34(+)CD38(+), and
  (c) Lin(−)CD34(−).

9. The method according to claim 8, wherein the cell fraction (a) is a leukemia stem cell.

10. The method according to claim 8, wherein the cell fraction (b) or (c) is a blast cell.

11. The method according to claim 7, wherein the tumor is lymphoma, myelodysplastic syndromes, acute myeloid leukemia or chronic myeloid leukemia.

12. The method according to claim 7, wherein the anti-TIM-3 antibody is an antibody which has a constant region originated from a human species.

13. The method according to claim 7, wherein the anti-TIM-3 antibody is at least one antibody selected from the group consisting of a monoclonal antibody, a chimeric antibody, a humanized antibody and a human antibody.

14. The method according to claim 7, wherein the anti-TIM-3 monoclonal antibody is an antibody having ADCC activity and/or CDC activity.

15. The method according to claim 1, wherein the cell fraction further comprises (c) Lin(−)CD34(+)CD38(−).

16. The method according to claim 1, wherein the cell fraction (a) or (b) is a blast cell.

17. The method according to claim 15, wherein the cell fraction (c) is a leukemia stem cell.

18. The method according to claim 15, wherein the cell fraction is a cell fraction selected from the group consisting of (a) and (b), (a) and (c), (b) and (c), and (a), (b) and (c).

* * * * *

SEQUENCE LISTING

```
<160> NUMBER OF SEQ ID NOS: 28

<210> SEQ ID NO 1
<211> LENGTH: 301
<212> TYPE: PRT
<213> ORGANISM: Homo sapiens

<400> SEQUENCE: 1
```

```
Met Phe Ser His Leu Pro Phe Asp Cys Val Leu Leu Leu Leu Leu
1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Gly Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
            290                 295                 300

<210> SEQ ID NO 2
<211> LENGTH: 200
<212> TYPE: PRT
<213> ORGANISM: Homo sapiens

<400> SEQUENCE: 2

Met Phe Ser His Leu Pro Phe Asp Cys Val Leu Leu Leu Leu Leu Leu
1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
50                  55                  60

Asn Val Val Leu Arg Thr Asp Glu Arg Asp Val Asn Tyr Trp Thr Ser
```

```
            65                  70                  75                  80
Arg Tyr Trp Leu Asn Gly Asp Phe Arg Lys Gly Asp Val Ser Leu Thr
                    85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
                115                 120                 125

Ile Lys Pro Ala Lys Val Thr Pro Ala Pro Thr Arg Gln Arg Asp Phe
        130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg
        195                 200

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
gccaccatgt tttcacatct tccctt                                            26

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ctatggcatt gcaaagcgac                                                   20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
taatacgact cactataggg                                                   20

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6
catacgattt aggtgacact atag                                              24

<210> SEQ ID NO 7
<211> LENGTH: 21
<212> TYPE: DNA
<213> ORGANISM: Artificial
```

```
<220> FEATURE:
<223> OTHER INFORMATION: primer

<400> SEQUENCE: 7
tcaaagtaga cggcatcgca g                                              21

<210> SEQ ID NO 8
<211> LENGTH: 18
<212> TYPE: DNA
<213> ORGANISM: Artificial
<220> FEATURE:
<223> OTHER INFORMATION: primer

<400> SEQUENCE: 8
gcattgcaaa gcgacaac                                                  18

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
tcaaagtaga cggcatcgca g                                              21

<210> SEQ ID NO 10
<211> LENGTH: 18
<212> TYPE: DNA
<213> ORGANISM: Artificial
<220> FEATURE:
<223> OTHER INFORMATION: primer

<400> SEQUENCE: 10
actctggagc aaccatca                                                  18

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
tcaaagtaga cggcatcgca g                                              21

<210> SEQ ID NO 12
<211> LENGTH: 27
<212> TYPE: DNA
<213> ORGANISM: Artificial
<220> FEATURE:
<223> OTHER INFORMATION: primer

<400> SEQUENCE: 12 tttctagat ctgatggttg ctccaga                                         27

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
taatacgact cactataggg                                                20
```

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
ttttctagat ctgatggttg ctccaga                                27

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
taatacgact cactataggg                                         20

<210> SEQ ID NO 16
<211> LENGTH: 18
<212> TYPE: DNA
<213> ORGANISM: Artificial
<220> FEATURE:
<223> OTHER INFORMATION: primer

<400> SEQUENCE: 16
actctggagc aaccatca                                           18

<210> SEQ ID NO 17
<211> LENGTH: 1336
<212> TYPE: DNA
<213> ORGANISM: Artificial
<220> FEATURE:
<223> OTHER INFORMATION: insert

<400> SEQUENCE: 17
gattgccacc atgttttcac atcttccctt tgactgtgtc ctgctgctgc tgctgctact    60
acttacaagg tcctcagaag tggaatacag agcggaggtc ggtcagaatg cctatctgcc   120
ctgcttctac accccagccg ccccagggaa cctcgtgccc gtctgctggg gcaaaggagc   180
ctgtcctgtg tttgaatgtg gcaacgtggt gctcaggact gatgaaaggg atgtgaatta   240
ttggacatcc agatactggc taaatgggga tttccgcaaa ggagatgtgt ccctgaccat   300
agagaatgtg actctagcag acagtgggat ctactgctgc cggatccaaa tcccaggcat   360
aatgaatgat gaaaaattta acctgaagtt ggtcatcaaa ccagccaagg tcaccctgc    420 accgactcgg cagagagact tcactgcagc ctttccaagg atgcttacca ccagggaca    480 tggcccagca gagacacaga cactggggag cctccctgat ataaatctaa cacaaatatc   540
cacattggcc aatgagttac gggactctag attggccaat gacttacggg actctggagc   600
aaccatcaga tctagagcag actacaagga cgacgatgac aagactagtg acaaaactca   660
cacatgccca ccgtgcccag cacctgaact cctgggggga ccgtcagtct tcctcttccc   720
cccaaaaccc aaggacaccc tcatgatctc ccggacccct gaggtcacat gcgtggtggt   780
ggacgtgagc cacgaagacc ctgaggtcaa gttcaactgg tacgtggacg gcgtggaggt   840
gcataatgcc aagacaaagc cgcgggagga gcagtacaac agcacgtacc gtgtggtcag   900
cgtcctcacc gtcctgcacc aggactggct gaatggcaag gagtacaagt gcaaggtctc   960
caacaaagcc ctcccagccc ccatcgagaa aaccatctcc aaagccaaag ggcagccccg  1020

```
agaaccacag gtgtacaccc tgcccccatc ccgggaggag atgaccaaga accaggtcag    1080
cctgacctgc ctggtcaaag gcttctatcc cagcgacatc gccgcggagt gggagagcaa    1140
tgggcagccg gagaacaact acaagaccac gcctcccgtg ctggactccg acggctcctt    1200
cttcctctac agcaagctca ccgtggacaa gagcaggtgg cagcagggga acgtcttctc    1260
atgctccgtg atgcatgagg ctctgcacaa ccactacacg cagaagagcc tctccctgtc    1320
tccgggtaaa tgatga                                                    1336
```

<210> SEQ ID NO 18
<211> LENGTH: 26
<212> TYPE: DNA
<213> ORGANISM: Artificial
<220> FEATURE:
<223> OTHER INFORMATION: primer

<400> SEQUENCE: 18

```
gccaccatgt tttcacatct tccctt                                         26
```

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19

```
gtccttgtag tctctgatgg ttgctccaga                                     30
```

<210> SEQ ID NO 20
<211> LENGTH: 26
<212> TYPE: DNA
<213> ORGANISM: Artificial
<220> FEATURE:
<223> OTHER INFORMATION: primer

<400> SEQUENCE: 20

```
gccaccatgt tttcacatct tccctt                                         26
```

<210> SEQ ID NO 21
<211> LENGTH: 39
<212> TYPE: DNA
<213> ORGANISM: Artificial
<220> FEATURE:
<223> OTHER INFORMATION: primer

<400> SEQUENCE: 21

```
aaaagcggcc gctcacttgt cgtcatcgtc cttgtagtc                           39
```

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22

```
taatacgact cactataggg                                                20
```

<210> SEQ ID NO 23
<211> LENGTH: 24
<212> TYPE: DNA
<213> ORGANISM: Artificial
<220> FEATURE:

<223> OTHER INFORMATION: primer

<400> SEQUENCE: 23
catacgattt aggtgacact atag                                          24

<210> SEQ ID NO 24
<211> LENGTH: 26
<212> TYPE: DNA
<213> ORGANISM: Artificial
<220> FEATURE:
<223> OTHER INFORMATION: primer

<400> SEQUENCE: 24
gccaccatgt tttcacatct tccctt                                        26

<210> SEQ ID NO 25
<211> LENGTH: 18
<212> TYPE: DNA
<213> ORGANISM: Artificial
<220> FEATURE:
<223> OTHER INFORMATION: primer

<400> SEQUENCE: 25
tagaaggcac agtcgagg                                                 18

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
taatacgact cactataggg                                               20

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
tagaaggcac agtcgagg                                                 18

<210> SEQ ID NO 28
<211> LENGTH: 645
<212> TYPE: DNA
<213> ORGANISM: Artificial
<220> FEATURE:
<223> OTHER INFORMATION: synthetic insert

<400> SEQUENCE: 28
gggaattcga ttgccaccat gttttcacat cttcccttttg actgtgtcct gctgctgctg     60
ctgctactac ttacaaggtc ctcagaagtg aatacagag cggaggtcgg tcagaatgcc    120 tatctgcccct gcttctacac cccagccgcc cagggaacc tcgtgcccgt ctgctggggc    180
aaaggagcct gtcctgtgtt tgaatgtggc aacgtggtgc tcaggactga tgaaagggat    240
gtgaattatt ggacatccag atactggcta aatggggatt ccgcaaagg agatgtgtcc    300 ctgaccatag agaatgtgac tctagcagac agtgggatct actgctgccg gatccaaatc    360
ccaggcataa tgaatgatga aaaatttaac ctgaagttgg tcatcaaacc agccaaggtc    420
acccctgcac cgactcggca gagagacttc actgcagcct ttccaaggat gcttaccacc    480

```
aggggacatg gcccagcaga gacacagaca ctggggagcc tccctgatat aaatctaaca        540
caaatatcca cattggccaa tgagttacgg gactctagat tggccaatga cttacgggac        600
tctggagcaa ccatcagaga ctacaaggac gatgacgaca agtga                        645
```